US 8,251,055 B2

United States Patent
Srinivasan et al.

(10) Patent No.: US 8,251,055 B2
(45) Date of Patent: *Aug. 28, 2012

(54) CONTINUOUS HIGH PRESSURE DELIVERY SYSTEM

(75) Inventors: Sudarsan Srinivasan, Glen Allen, VA (US); David Ammann, Alpharetta, GA (US); Donald Brookman, Richmond, VA (US); Niranjan Maharajh, Richmond, VA (US); Gary Grollimund, Chesterfield, VA (US); F. Murphy Sprinkel, Jr., Glen Allen, VA (US); Douglas D. McRae, Chesterfield, VA (US)

(73) Assignee: Philip Morris USA Inc., Richmond, VA (US)

( * ) Notice: Subject to any disclaimer, the term of this patent is extended or adjusted under 35 U.S.C. 154(b) by 1303 days.

This patent is subject to a terminal disclaimer.

(21) Appl. No.: 11/866,283

(22) Filed: Oct. 2, 2007

(65) Prior Publication Data

US 2008/0110458 A1    May 15, 2008

Related U.S. Application Data

(60) Provisional application No. 60/849,038, filed on Oct. 2, 2006.

(51) Int. Cl.
*A61M 11/04* (2006.01)
(52) U.S. Cl. ......... 128/200.14; 128/203.12; 128/203.26; 128/204.17
(58) Field of Classification Search ............. 128/200.14, 128/200.24, 203.12, 203.16, 203.17, 203.26, 128/203.27, 204.17
See application file for complete search history.

(56) References Cited

U.S. PATENT DOCUMENTS

| | | | |
|---|---|---|---|
| 4,575,609 A | 3/1986 | Fassel et al. |
| 4,960,992 A | 10/1990 | Vestal et al. |
| 5,743,251 A | 4/1998 | Howell et al. |
| 6,003,512 A | 12/1999 | Gerde |

(Continued)

FOREIGN PATENT DOCUMENTS

| | | |
|---|---|---|
| DE | 1077828 B | 3/1960 |
| EP | 0624379 A | 11/1994 |
| FR | 2543442 A | 10/1984 |
| WO | WO97/42993 A | 11/1997 |
| WO | WO01/38514 A | 5/2001 |
| WO | WO03/053502 A | 7/2003 |
| WO | WO2005/003547 A | 1/2005 |
| WO | WO2007/076064 A | 7/2007 |

OTHER PUBLICATIONS

International Preliminary Report on Patentability mailed Apr. 16, 2009 for PCT/US2007/080219. International Search Report and Written Opinion dated Aug. 14, 2008 for PCT/US2007/080219.
Japanese Office Action issued by the Japanese Patent Office on Apr. 27, 2012 in corresponding Japanese Patent Application No. 2009-531563.

*Primary Examiner* — Justine Yu
*Assistant Examiner* — LaToya M. Louis
(74) *Attorney, Agent, or Firm* — Buchanan Ingersoll & Rooney PC

(57) ABSTRACT

A drug delivery system, which includes an aerosol generator unit, a pumping unit, a flow tube, at least one condensate collector and an aerosol transition adapter. The aerosol generator forms an aerosol from a liquid formulation, which is partially volatilized. The pumping unit supplies the liquid formulation to the aerosol generator unit and a flow tube having an inlet end in fluid communication with an outlet of the aerosol generator unit and an outlet adapted for connection to a patient interface, which supplies ventilation gas to a patient's lungs. The system also includes at least one condensate collector adapted to collect condensed liquid or liquid produced by the aerosol generator unit, and a transition adapter arranged to mix aerosol produced by the aerosol generator unit with heated air or ventilation gas and direct the mixed aerosol into the inlet end of the flow passage.

21 Claims, 18 Drawing Sheets

U.S. PATENT DOCUMENTS

| | | |
|---|---|---|
| 6,501,052 B2 | 12/2002 | Cox et al. |
| 6,640,050 B2 | 10/2003 | Nichols et al. |
| 6,772,757 B2 | 8/2004 | Sprinkel, Jr. |
| 6,804,458 B2 | 10/2004 | Sherwood et al. |
| 7,167,776 B2 | 1/2007 | Maharajh et al. |
| 7,428,902 B2 | 9/2008 | Du et al. |
| 7,802,569 B2 * | 9/2010 | Yeates et al. ............. 128/203.12 |
| 2003/0108342 A1 * | 6/2003 | Sherwood et al. ............ 392/397 |
| 2004/0223918 A1 | 11/2004 | Pham et al. |
| 2005/0205084 A1 * | 9/2005 | Gupta et al. ............. 128/200.14 |
| 2005/0235991 A1 | 10/2005 | Nichols et al. |
| 2006/0163570 A1 | 7/2006 | Renn et al. |
| 2009/0310950 A1 | 12/2009 | Maharajh et al. |

* cited by examiner

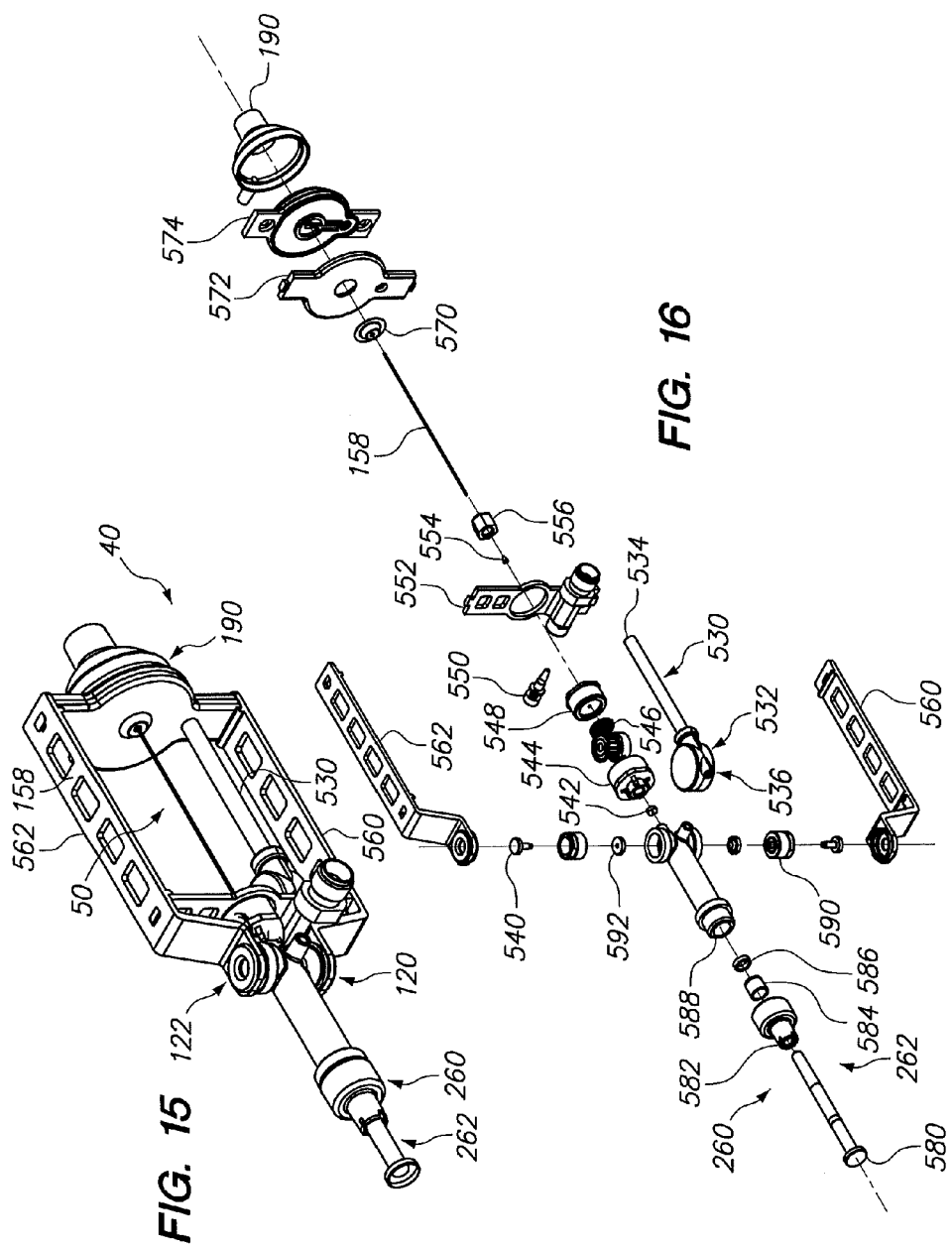

FIG. 18

CONTINUOUS HIGH PRESSURE DELIVERY SYSTEM

CROSS-REFERENCE TO RELATED APPLICATION

This application claims priority to U.S. Patent Provisional Application No. 60/849,038, filed Oct. 2, 2006, which is incorporated herein by this reference in its entirety.

BACKGROUND

Capillary aerosol technology and capillary aerosol generators have been described in U.S. Pat. No. 5,743,251, the contents of which are hereby incorporated by reference in their entirety.

SUMMARY

In accordance with one embodiment, a drug delivery system, comprises: an aerosol generator unit wherein a liquid formulation is partially volatilized to form an aerosol; a pumping unit adapted to supply a liquid formulation to the aerosol generator unit; a flow passage having an inlet end in fluid communication with an outlet of the aerosol generator unit and an outlet adapted for connection to a patient interface which supplies ventilation gas to a patient's lungs; at least one condensate collector adapted to collect condensed liquid or liquid produced by the aerosol generator unit; and a transition adapter arranged to mix aerosol produced by the aerosol generator unit with heated air or ventilation gas and directs the mixed aerosol into the inlet end of the flow passage.

In accordance with a further embodiment, a drug delivery system, comprises: an aerosol generator unit wherein a liquid formulation is partially volatilized to form an aerosol; a pumping unit adapted to supply a liquid formulation to the aerosol generator unit at high pressures; a disposable assembly that operates at high pressures; a flow passage having an inlet end in fluid communication with an outlet of the aerosol generator unit and an outlet adapted for connection to a patient interface which supplies ventilation gas to a patient's lungs; at least one condensate collector adapted to collect condensed liquid or liquid produced by the aerosol generator unit; and a transition adapter arranged to mix aerosol produced by the aerosol generator unit with heated air or ventilation gas and directs the mixed aerosol into the inlet end of the flow passage.

In accordance with another embodiment, an apparatus to produce an aerosol comprises: a heated capillary aerosol generator; an arrangement to produce a flow of heated air or ventilation gas; and a mixer to mix the flow of heated air or ventilation gas with an output of the heated capillary aerosol generator.

In accordance with a further embodiment, a method of producing an aerosol comprises: generating an aerosol with a heated capillary; and admixing heated air or ventilation gas with the generated aerosol so as to reduce condensation.

In accordance with another embodiment, a method of delivering an aerosol of a drug continuously to a remote location comprises: generating an aerosol of the drug with a heated capillary; admixing heated air or ventilation gas with the generated aerosol so as to produce a heated aerosol of increased flow rate; and communicating said heated aerosol along a passage to said remote location.

BRIEF DESCRIPTION OF THE DRAWINGS

FIG. 15 is a perspective view of the disposable assembly of the drug delivery system of FIG. 11.

FIG. 16 is an exploded view of the disposable assembly of FIG. 15.

FIG. 18 is a chart of a drug delivery system showing drug concentration (milligrams per liter of air) versus flow rate (liter per minute) in accordance with an embodiment.

DETAILED DESCRIPTION

Figure 1:
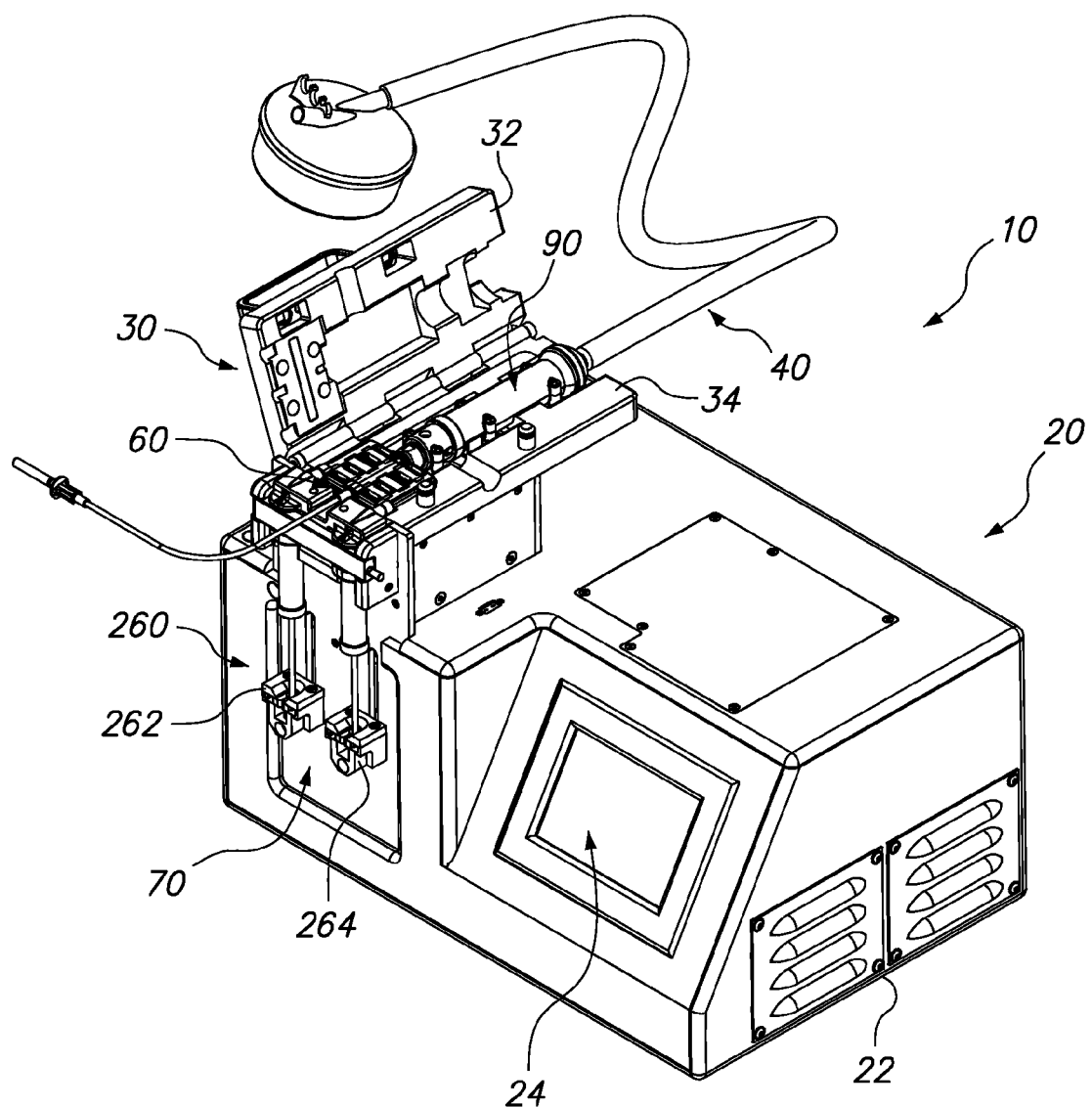
FIG. 1 is a perspective view of a drug delivery system in accordance with one embodiment having a disposable assembly housing in an open position.

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols can be generated from a heated capillary aerosol generator by feeding a solution or suspension in a liquid state to a capillary while heating the capillary sufficiently such that the solution (or the carrier portion of the suspension) is volatilized, so that upon discharge from the heated capillary, the solution (or suspension) is in the form of an aerosol. The length of the capillary can depend on heat requirements dictated by, among other factors, the composition of the aerosol to be generated. A potential problem associated with directly heated capillary aerosol generators is broad temperature variations inside the capillary tube that may lead to overheating and substandard aerosol formation, resulting in clogging of the capillary tube and/or failure of a capillary aerosol generator.

In accordance with one embodiment, the aerosol generating system can be used to aspirate a liquid material or formulation from a disposable assembly (i.e., a container closure system), and dispense it through an aerosol generator or capillary tube sub-assembly for delivery of a continuous aerosolization.

In accordance with another embodiment, a thermally conductive heater block encases a capillary passage through a block, such as a capillary tube, such that the thermally conductive heater block maximizes heat transfer substantially evenly and uniformly from the thermally conductive heater block to the capillary tube. In accordance with one embodiment, the thermally conductive heater block is preferably a stainless steel block having an upper half and a lower half, which is adapted to receive an aerosol generator in the form of a capillary tube, and heater cartridges and electrical leads attached to the heater cartridges. The electrical leads are connected to a power source. The power source is selected in view of the characteristics of the components of the aerosol generator.

In accordance with a further embodiment, the drug delivery system is able to provide a method for controlling the fluid flow from a source to an output at high pressure and to allow fluid flow and stop flow under high pressure (i.e., at least 2000 psi) in a disposable and low cost system.

In operation, the electrical leads transfer power from the power source to the heater cartridges that are inserted into the thermally conductive heater block, thereby heating the thermally conductive heater block. When heated, the thermally conductive heater block transfers heat to the aerosol generator or capillary tube and thus substantially evenly and uniformly heats the capillary tube to a temperature sufficient to at least partially volatilize the liquid material or the liquid formulation that is introduced to the heated capillary tube. For example, the at least partially volatilized liquid material or liquid formulation can be driven through a restrictor to atomize the liquid material or formulation. The volatilized material mixes with ventilation gas supplied by a heated sheath gas source within an aerosol confinement member at a distal end of the heater block and forms an aerosol.

Liquid material is preferably introduced into the capillary tube through an inlet of the capillary tube connected to a source of liquid material. The volatilized material is driven out of the capillary tube through the outlet of the capillary tube, i.e., the back pressure of the liquid from the source of liquid material causes the liquid to be ejected from the outlet.

Electrical current passed directly through a conductive capillary tube may provide uneven heating across the length of the capillary tube, with temperature variations inside the capillary tube on the order of about 50 degrees Celsius (° C.) to 100 degrees Celsius (° C.). In contrast, a heater block and heated capillary aerosol generator provides substantially even and uniform heating across the heated length of the capillary tube. Because the thermally conductive material of the heater block has a mass that is preferably at least about ten times the mass of the capillary tube and the heater cartridges are preferably positioned longitudinally within the heater block, the temperature inside the capillary tube preferably varies by less than about 5° C. Further, by providing electrical energy to the heater cartridges in a controlled manner, the temperature inside the capillary tube can be accurately maintained.

Since the heater block provides substantially even and uniform heat distribution along the length of the capillary tube, liquid material or volatilized liquid material can be heated to a desired temperate range without overheating the liquid. Overheating can impair aerosol formation and/or result in clogging of the capillary tube and/or failure of an aerosol generator.

In accordance with one embodiment, the drug delivery system includes an aerosol generator and a heater block, wherein the temperature of the heater block and the thermally conductive material is heated to and maintained at an operating temperature (i.e., a temperature at which liquid material in the capillary tube is volatilized), which is in the range of about 250.degree. C. to 400.degree. C. Accordingly, it would be desirable to provide a constant, uniform temperature source for a medical or drug delivery system having an aerosol generator, and wherein a liquid formulation is partially volatilized to form an aerosol for inhalation.

FIG. 1 shows a perspective view of a drug delivery system 10 (or aerosol generation system) in accordance with one embodiment. As shown in FIG. 1, the drug delivery system 10 comprises a base unit 20, which is adapted to receive a disposable assembly 40 in the form of a sterile disposable fluid system. The base unit 20 is comprised of a housing 22, a disposable assembly housing 30 adapted to receive the disposable assembly 40, a compact reconfigurable input/output (I/O) controller assembly 36 (FIG. 3) and a user interface 24. The user interface 24 can be a touch screen panel as shown in FIG. 1, or other suitable interface system for input of information and receiving of operational data from the system 10.

The disposable assembly housing 30 is preferably comprised of a clam-shell like housing, which is adapted to receive the disposable assembly 40. The disposable assembly 40 preferably includes a heater block subassembly 90 with an aerosol generator unit 50 (FIG. 7) therein. As shown in FIG. 1, the disposable assembly housing 30 in the base unit 20 is comprised of an upper or first half 32 and a lower or second half 34, which is adapted to surround the disposable assembly 40 in a clam-shell configuration, including a handle for ease of opening and closing of the housing 30. The disposable assembly 40 fits within the lower or second half of the housing 30, and ensures that the components of the disposable assembly 40 are matched to their respective connections within the base unit 20.

In use, the heater block subassembly 90 has an indirect heating block 150 (FIG. 7), which encases an aerosol generator (or aerosol generating unit) 50, for heating a liquid material or liquid formulation, which is pumped through the aerosol generator unit 50 at a constant and continuous rate by a pumping unit 260. In accordance with an embodiment, the pumping unit 260 includes two syringe pumps 262, 264 and a valving arrangement or assembly 60 operable to supply liquid formulation into an inlet of one syringe pump 262, 264 during delivery of liquid formulation to the aerosol generator unit 50 by the other syringe pump 262, 264.

Figure 2:
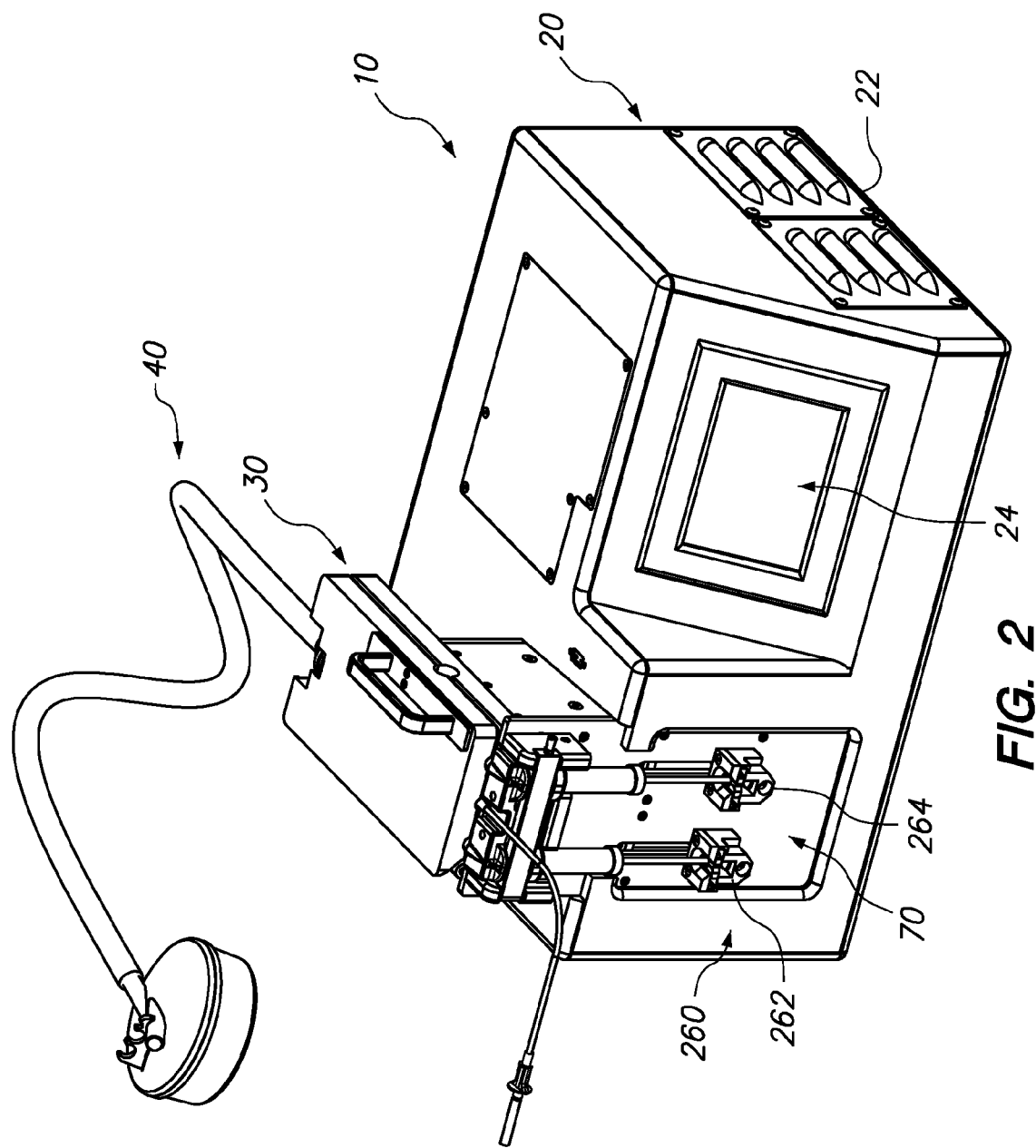
FIG. 2 is a perspective view of the drug delivery system of FIG. 1 with the disposable assembly housing in a closed position.

FIG. 2 shows a perspective view of the drug delivery system 10 of FIG. 1 with the disposable assembly housing 30 in a closed position. The disposable assembly 40 is attachable to a source of liquid material or liquid formulation 136 (FIG. 5), which is partially vaporized to form an aerosol. As shown in FIGS. 1 and 2, the housing 22, the disposable assembly housing 30, the compact reconfigurable input/output (I/O) controller assembly 36 and the user interface 24 are preferably part of and/or incorporated into the base unit 20 of the aerosol generating system 10. It can be appreciated that since the disposable assembly 40 is disposable, the aerosol generating system 10 is much more attractive from a cost standpoint, since the system 10 can be reused in a hospital setting.

In accordance with one embodiment, the capillary aerosol generating system 10 is adapted to continuously deliver a liquid material or liquid formulation 136 as an aerosol, wherein the liquid material or formulation 136 is heated in an aerosol generator 50 to partially volatilize at least some of the liquid material or liquid formulation 136. In accordance with a preferred embodiment, the liquid material or liquid formulation 136 is Surfaxin.® manufactured by Discovery Laboratories, Inc. In the formation of an aerosol, the liquid material or liquid formulation 136 is pumped through an aerosol generator 50 preferably in the form of a heated capillary tube. The aerosol generating system 10 can be comprised of a base unit 20 and wetted components including a sterile disposable fluid system or disposable assembly 40. In accordance with one embodiment, the base unit 20 preferably includes an enclosure or housing 22, a pumping unit 260 having a pair of syringe pumps 262, 264, a compact reconfigurable input/output (I/O) controller assembly 36 and a user interface 24.

The liquid material or liquid formulation 136 will preferably be a refrigerated formulations such as a surfactant, or other suitable material. The liquid material or liquid formulations 136 are preferably contained within a refrigerated dose packet 350 (FIG. 17) having an outer protective foil bag. The refrigerated liquid material or liquid formulation 136 is preferably heated using a hot plate/stirrer 300 (FIG. 17) or other suitable heating device to form a suitable formulation for delivery to the syringe assembly 70. It can be appreciated that these formulations 136 are usually quite viscous, although they comprise mostly water.

Figure 3:
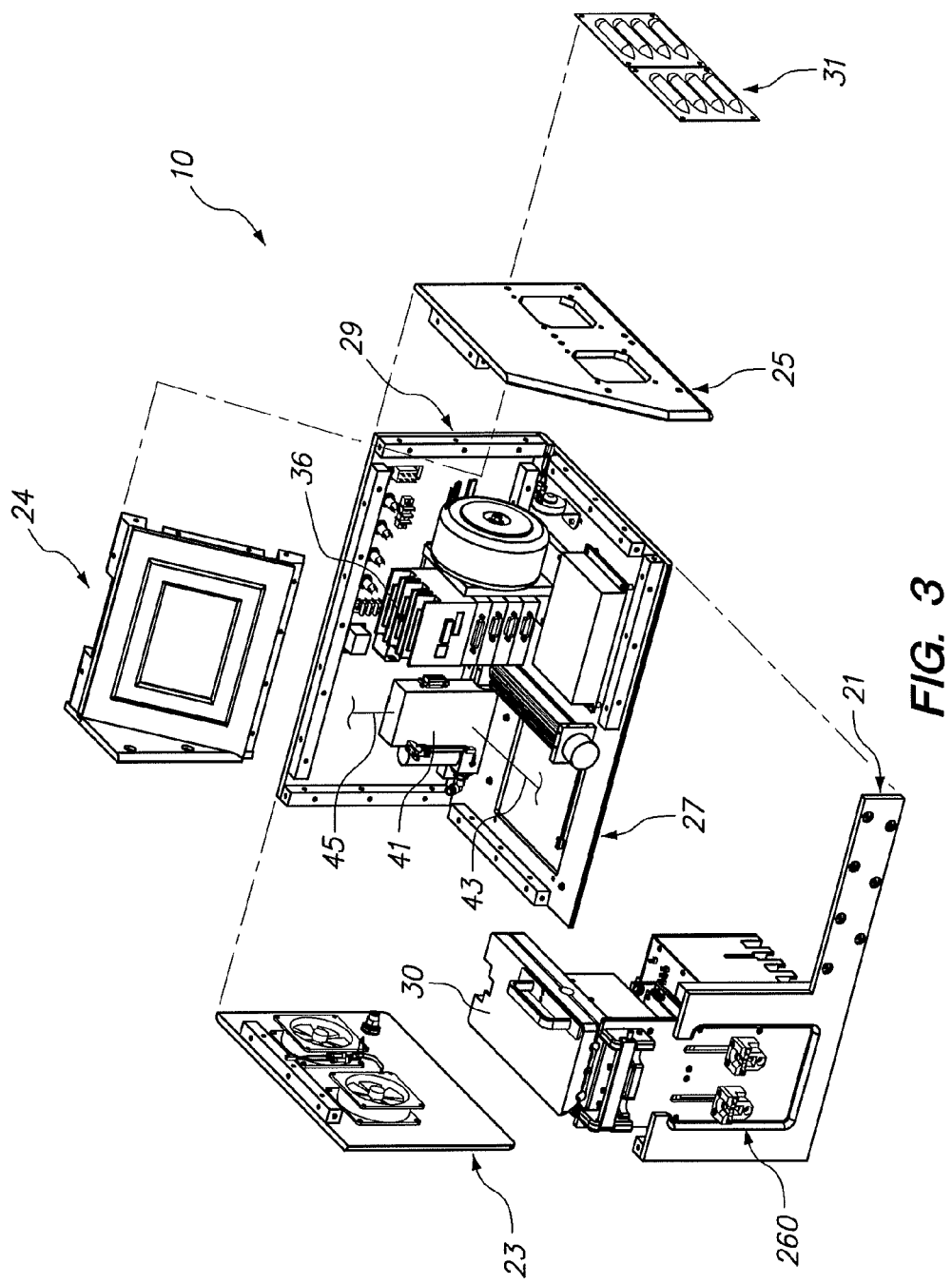
FIG. 3 is an exploded view of the drug delivery system of FIGS. 1 and 2.

FIG. 3 shows an exploded view of the drug delivery system 10 of FIGS. 1 and 2. As shown in FIG. 3, the drug delivery system 10, the housing 22 is comprised of a front panel assembly 21, a left side panel assembly 23, a right side panel assembly 25, a base panel assembly 27 and a back panel assembly 29, a vent panel assembly 31, a compact reconfigurable input/output (I/O) controller assembly 36 and a touch screen panel assembly 24. The base unit 20 is adapted to house the electric components, printed circuit boards (PCB), power source, flow controllers, thermocouple devices and controls, voltage control coil, motors, fans to cool the unit, and other related digital and electronic devices for operation of the drug delivery system 10. The system 10 can also include a flow controller 41 having a line 43 into the flow controller 41 from a source of pressurized gas (such as a pressurized ventilation gas line in a hospital room) and a line 45 from the flow controller 41 to an underside of the housing 30.

Figure 4:
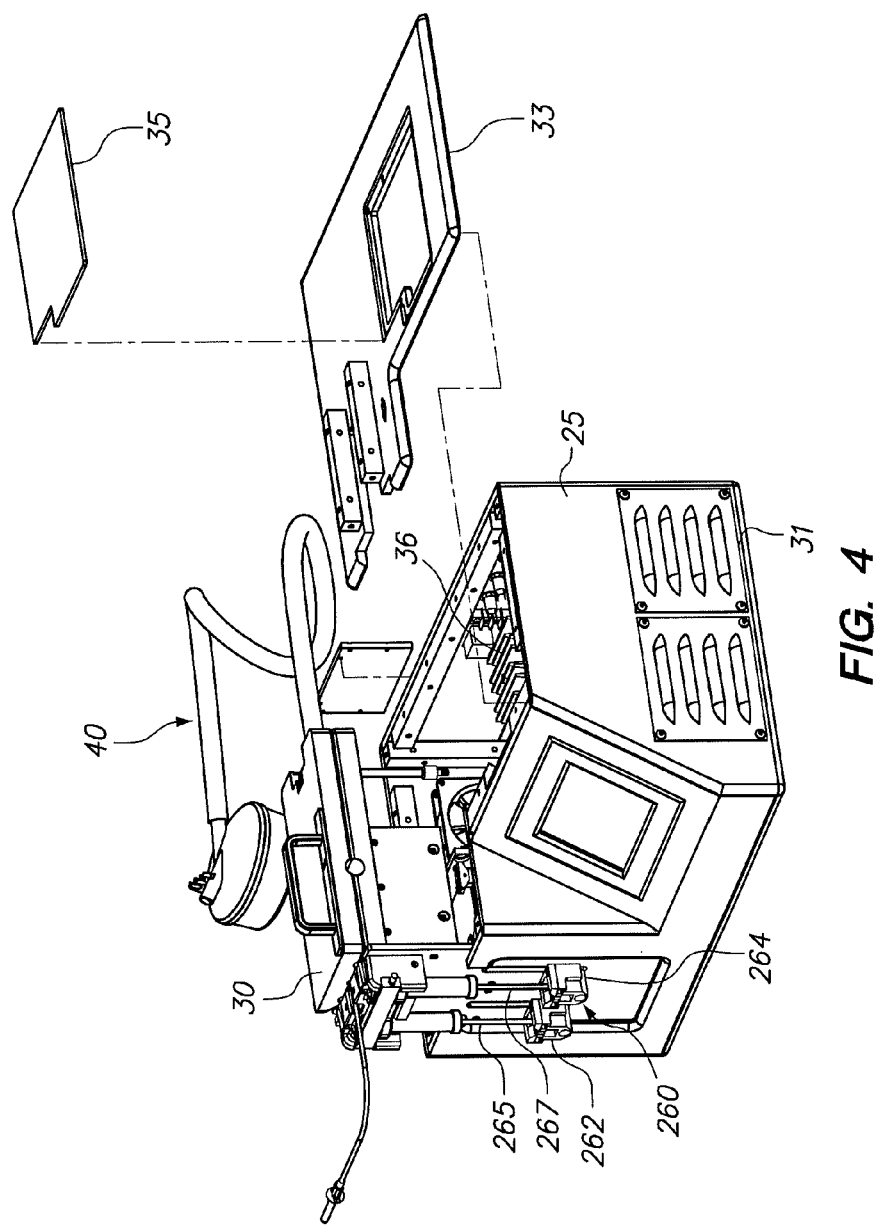
FIG. 4 is another exploded view of the drug delivery system.

FIG. 4 shows another exploded view of the drug delivery system 10. As shown in FIG. 4, the base unit 20 includes further includes a top panel assembly 33 and a top panel assembly cover 35. The base unit 20 also preferably includes a control system, such as a compact reconfigurable input/output (I/O) controller assembly 36, which is operable to activate the aerosol generator unit 50 and the pumping unit 260.

In accordance with one embodiment, the compact reconfigurable input/output (I/O) controller assembly 36 effects an initial filling of the syringe pumps 262, 264 via retraction of a first piston 265 of the first syringe pump 262 and a second piston 267 of the second syringe pump 264 while maintaining the first and third valves 116, 120 (FIG. 6) in an open position and the second and fourth valves 118, 122 in a closed position. The liquid formulation 136 is delivered to the aerosol generator unit 50 via advancement of the first piston 265 while maintaining the first and fourth valves 116, 122 in a closed position, and activating the second syringe pump 264 near the end of a delivery cycle of the first syringe pump 262 via advancement of the second piston 267 while maintaining the fourth valve 122 in an open position and the third valve 120 in a closed position. The refilling of the first syringe pump 262 is performed via retraction of the first piston 265 while maintaining the first valve 116 in an open position and the second valve 118 in a closed position, and activating the first syringe pump 262 near the end of the delivery cycle of the second syringe pump 264 via advancement of the first piston 265 while maintaining the second valve 118 in an open position and the first valve 116 in a closed position.

Figure 5:
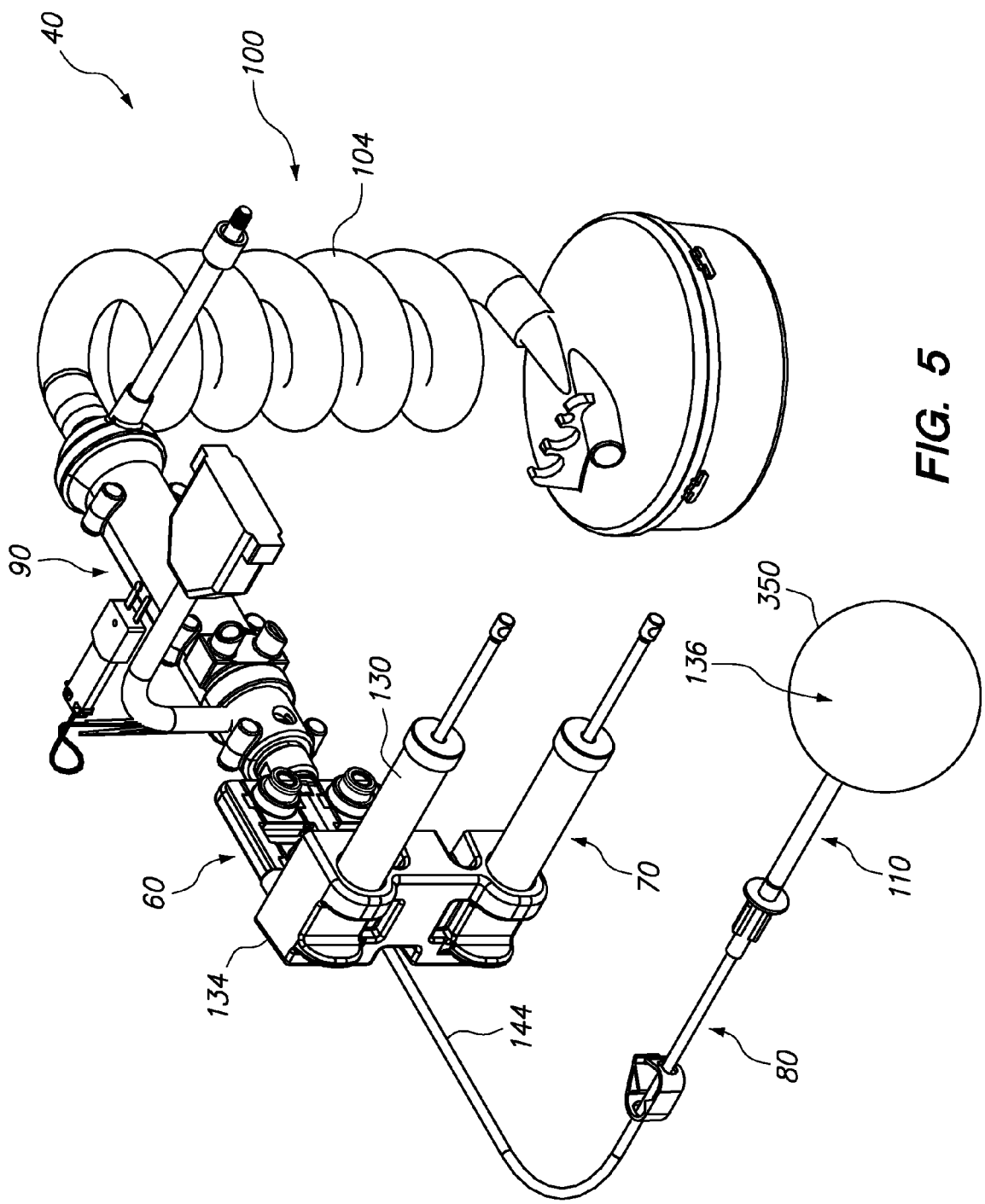
FIG. 5 is a perspective view of a disposable assembly of the drug delivery system of FIG. 1.

FIG. 5 shows a perspective view of the disposable assembly 40 (or sterile disposable fluid system). As shown in FIG. 5, the disposable assembly 40 preferably includes a valve assembly 60, a syringe assembly 70, an input fluid tube assembly 80, a heater block subassembly 90, and a fluid trap assembly 100. In accordance with a preferred embodiment, the disposable assembly 40 includes a combination of disposable and reusable parts. The disposable parts include a capillary flow tube 158 (FIG. 7) through which the liquid formulation 136 is ejected as an aerosol, and the wetted parts of the pumping unit 260, including a screening member (not shown) operable to trap particles in the liquid formulation 136 above a predetermined size. In accordance with a preferred embodiment, the screening member is located upstream of the inlet to the aerosol generator unit 50.

It can be appreciated that a fluidic element (not shown) can be positioned between the valve assembly 70 and the aerosol generation unit 50 to stabilize the nominal operating pressure within the capillary passage 158 of the aerosol generating unit 50. The fluidic element increases the threshold backpressure for aerosolization (i.e., the minimum pressure needed to keep the flow consistent and capillary wet) and reduces the pressure oscillation within the system as a result of the conversion of the liquid material or formulation 136 to vapor and large particles within the liquid material or formulation.

A patient interface in the form of a continuous positive airway pressure ventilator adaptor (e.g., nosepiece or mouthpiece) (not shown) can also be included with the disposable assembly 40. In accordance with one embodiment, the continuous positive airway pressure ventilator adaptor (e.g., nosepiece or mouthpiece) also includes a pharyngeal tube that cooperates with a ventilator. Mouthpieces for aerosol generators have been described in U.S. Pat. No. 6,701,922, the contents of which are hereby incorporated by reference in their entirety.

The system 10 also includes at least one condensate collector or fluid trap assembly 100 adapted to collect condensed liquid or liquid produced by the aerosol generator 50. The flow tube 104 includes an inlet end 105 in fluid communication with an outlet 191 of the aerosol generator 50 and an outlet (not shown) adapted for connection to a patient interface, which supplies ventilation gas to a patient's lungs.

Figure 6:
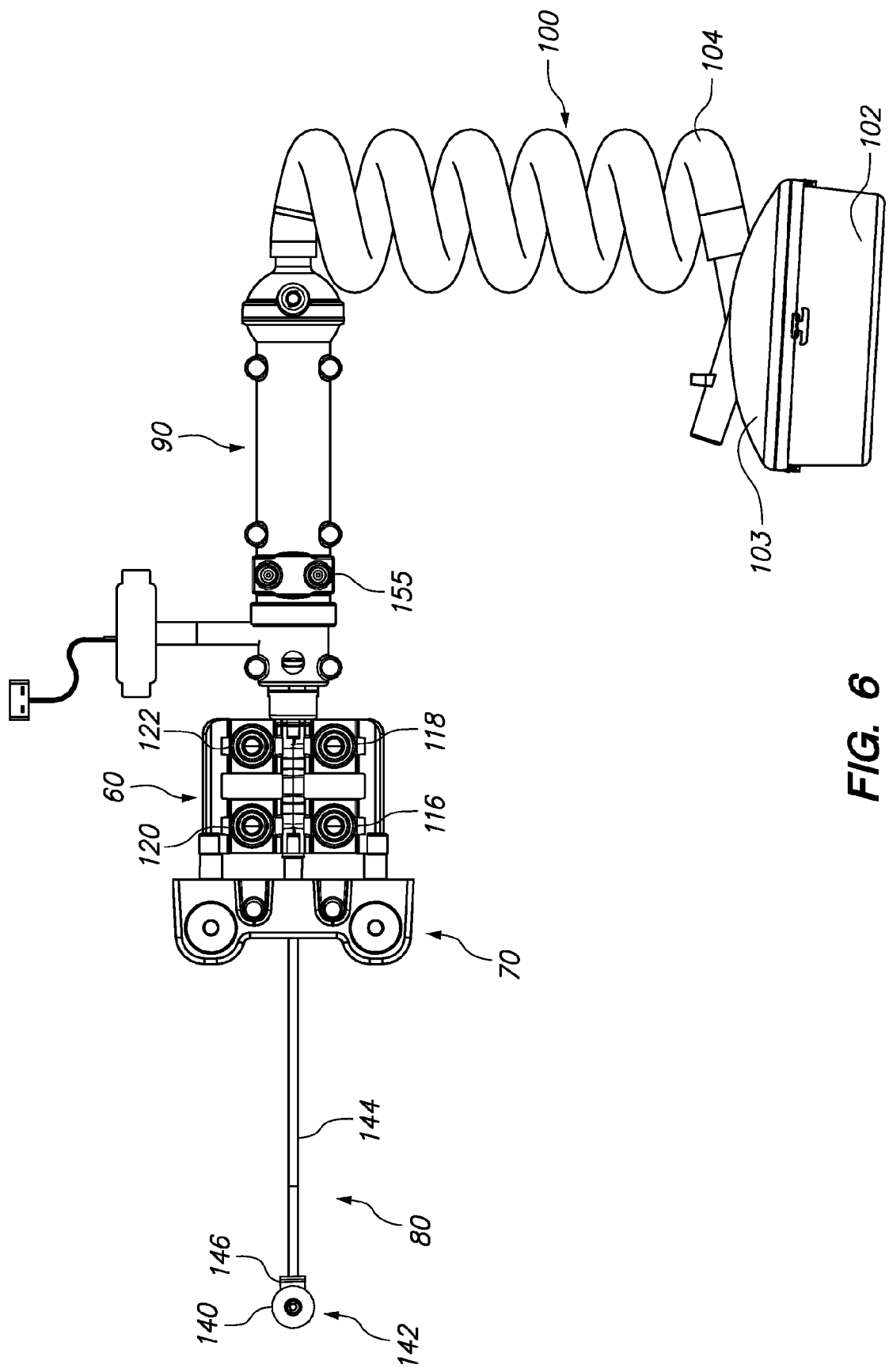
FIG. 6 is a side view of the disposable assembly of FIG. 5.

FIG. 6 shows a side view of the disposable assembly 40 as shown in FIG. 5. As shown in FIG. 6, the disposable assembly 40 includes a 4-valve assembly 60, a syringe assembly 70, an input fluid tube assembly 80, a heater block subassembly 90, and a fluid trap assembly 100. As shown in FIG. 6, the disposable assembly 40 also includes a pair of sheath gas inlets 155 on a lower surface of the heater block subassembly 90.

The at least one condensate collector or fluid trap assembly 100 includes a bowl or fluid trap 102, a bowl top 103 for the fluid trap 102, and a flow tube or tubing 104. The flow tube or tubing 104 is attachable to an additional tubing section (not shown), which is attachable to a patient interface in the form of a CPAP adaptor, nosepiece or mouthpiece.

Figure 7:
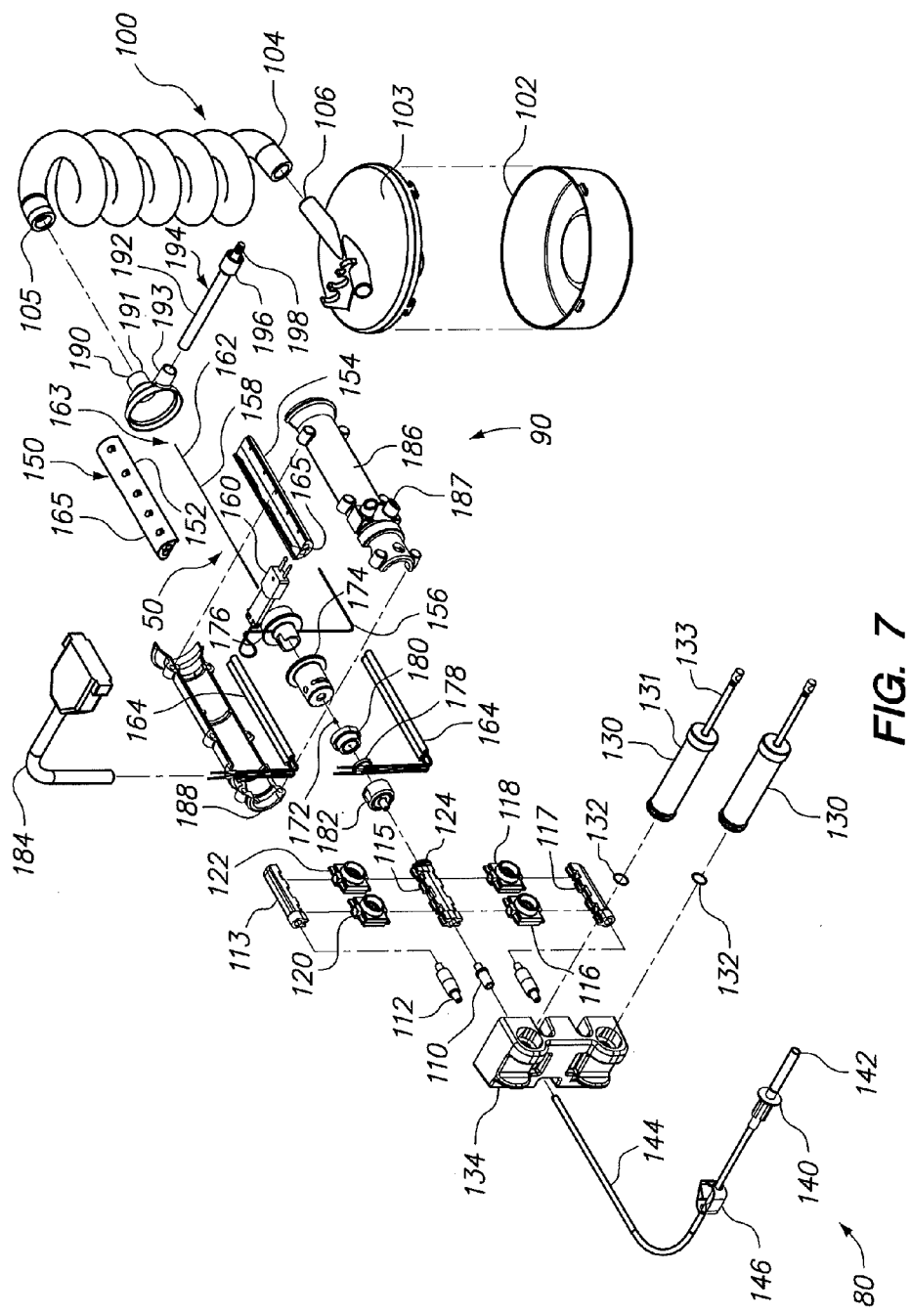
FIG. 7 is an exploded view of the disposable assembly of FIG. 5.

FIG. 7 shows an exploded view of the disposable assembly 40. As shown in FIG. 7, the valve assembly 60 includes an inlet 110 in the form of an input barb fitting, a pair of tubing adaptors 112, 114, a plurality of valves 116, 118, 120, 122, and an outlet or output port 124. The valve assembly 60 also includes a plurality of flow channel supports 113, 115, 117, which are attached to the pair of tubing adaptors 112, 114, the plurality of valves 116, 118, 120, 122, and the outlet or output port 124. The valve assembly 60 will preferably be controlled mechanically through a valve control assembly or control system.

The valving arrangement or valve assembly 60 as shown in FIG. 7 includes an inlet 110 which can be connected to a source of a liquid formulation 136, first and second flow paths in fluid communication with the inlet 110, an outlet or output port 124 in fluid communication with an inlet of the aerosol generator or aerosol generation unit 50, first and second valves 116, 118 along the first flow path and third and fourth valves 120, 122 along the second flow path, the valves 116, 118, 120, 122 arranged such that the first flow path supplies liquid formulation 136 to the first syringe pump 262 when the first valve 116 is open and the second valve 118 is closed, the second flow path supplies liquid formulation to the second syringe pump 264 when the third valve 120 is open and the second valve 118 is closed, the first flow path supplying liquid formulation to the aerosol generator 50 when the first valve 116 is closed and the second valve 118 is open, and the second flow path supplying liquid formulation to the aerosol generator 50 when the third valve 120 is closed and the fourth valve 122 is open.

The syringe assembly 70 is comprised of a pair of syringes 130, a pair of syringe O-rings 132 and a dual syringe block holder 134. The syringes 130 include a barrel 131 and a plunger (or rod) 133. The plunger or rod 133 of the syringes 130 is adapted to fit within the syringe pumps 262, 264 of the pumping unit 260. In accordance with one embodiment, the syringes 130 are preferably comprised of two 1 ml syringes, which are adapted to aspirate and dispense the liquid material or formulation 136 from the container closure system 350. However, it can be appreciated that other size syringes can be used depending on the different components and uses of the system 10.

The input fluid tube assembly 80 is comprised of a spike 140, a spike protector or tube 142, a spike tubing assembly 144, and a tubing clamp 146. As shown in FIG. 5, the syringe assembly 70 includes an input line 110 from the container closure system 136 (FIG. 7) and an output line 124 to the capillary tube, which is contained within the heater block subassembly 90. After the initial priming cycle, at any given time, one syringe 130 will dispense and the other syringe 130 will aspirate. Each of the syringes 130 will have two halves, one for the container closure system 350 and the other to the capillary tube 158 or aerosol generator unit 50.

The syringe pumps 262, 264 (FIG. 2) will preferably include drive trains and control electronics to allow simultaneous operation of the dual syringes 130 in order to dispense liquid material or liquid formulation 136 continuously. The programmable automation controller will also preferably generate the signals for opening and closing of the valves 116, 118, 120, 122. It can be appreciated that pump parameters such as dispense rate, aspiration rate, handshake parameters, etc. will preferably reside local to the automation controller and can be changed by an independent user interface such a laptop computer or other suitable input device. The functions of priming, start, stop, and pause for the pumping unit 260 can also be generated by the main user interface and will be communicated through a programmable automation controller.

In accordance with one embodiment, the pumping unit 260 should be able to support backpressures of up to at least 2,000 psi, and more preferably up to 3,000 to 4,000 psi. In addition, the syringe pumps 262, 264 are preferably mounted in a fluid resistant enclosure, and can include a force sensor on each syringe-mounting bracket to monitor the plunger force during fluid delivery. The syringes 130 can be installed with a minimum of mechanical locking to the pump, such that the syringes 130 may not require wire connections on the syringe end of the pump (where the mechanical valves will be placed). In addition, the programmable automation controller can include a flow meter (not shown) within the dual syringe pumps to control the sheath gas flow rate before it enters the disposal. The pumping capacity of the syringe pumps 262, 264 facilitate handling of highly viscous formulations 136 such as Surfaxin®.

The heater block subassembly 90 includes a heater block 150 comprised of an upper or top assembly 152 and a lower or bottom assembly 154, a thermocouple 156, and an aerosol generator unit 50 in the form of a capillary tube 158. The aerosol generator unit 50 includes a capillary passage in which the liquid formulation 136 is at least partially volatilized, a heater body or block assembly 150 operable to heat the capillary passage to a temperature range effective to at least partially volatilize liquid formulation in the capillary passage or tube 158, and at least one ventilation gas passage arranged such that air is heated by the heater body or block 150 and the heated air is combined with the aerosols produced by the aerosol generator unit 50.

As shown in FIG. 7, the heater body or heater block 150 is comprised of two assemblies (i.e., an upper assembly and a lower assembly) 152, 154, which includes at least one longitudinally extending bore 165 and more preferably two (2) longitudinally extending bores 165 adapted to receive a heater element 164. The heater element 164 is preferably 30-watt heater cartridges; however, it can be appreciated that any suitable watt heater cartridge can be used. It can also be appreciated that the heater block subassembly 90 can include any suitable heating system including heated coils and/or wires. The two assemblies 152, 154 are preferably constructed of a thermally conductive material, such as stainless steel or other suitable material. In use, the thermally conductive material forming the heater body or heater block 150 is heated to and maintained at an operating temperature to volatilize at least some of the liquid material therein.

The thermocouple 156 is preferably incorporated into the heater block subassembly 90. In accordance with one embodiment, the thermocouple 156 is preferably incorporated into either the upper and lower assemblies 152, 154, such that the placement of the thermocouple 156 ensures accurate temperature monitoring. By utilizing the thermocouple 156 as a feedback device, a closed loop temperature control system can be used to control the temperature of the capillary tube 158.

The capillary tube 158 can include a feed tube end or proximal end 160, and a domed capillary end or distal end 162. The capillary tube 158 preferably has an inside diameter in the range of about 0.05 to 0.53 millimeters, and more preferably in the range of about 0.1 to 0.2 millimeters. The feed tube end 160 is preferably circular in cross-section with a domed capillary end 163 on the distal end 162 of the capillary tube 158. A particularly preferred inside diameter of the capillary tube 158 is approximately 0.1905 mm (or 0.0075 inches). In accordance with one embodiment, the capillary tube 158 has a length of approximately 90 mm to 120 mm, and more preferably 100 mm to 110 mm. However, it can be appreciated that the length of the capillary tube 158 is based on the flow rate of the liquid formulation or liquid material 138 within the capillary tube 158.

In accordance with one embodiment, the capillary tube 158 is a tipped capillary as described in U.S. Publication No. 20050235991, the contents of which are hereby incorporated by reference in their entirety. As described in U.S. Publication No. 20050235991, the capillary tube 158 can include a constriction in the form of a domed capillary end or formed tip 163 at the outlet or distal end 162 of the flow passage. In accordance with a preferred embodiment, the distal end 162 of the flow passage has an opening in the range of 1000 to 5000 square microns and more preferably the opening is in the range of 2000 to 3000 square microns.

It can be appreciated that the domed capillary end or formed tip 163 can be formed by any suitable technique. For example, the domed capillary end or formed tip 163 can be formed by inserting a mandrel, such as a cylindrical wire, a desired distance into the flow passage, and then deforming the capillary tube 158 around the mandrel, such as by crimping. The mandrel can have a desired cross-sectional shape and cross-sectional area that define the desired size and shape of the flow section. In alternative embodiment, the tip 163 of the capillary tube 158 can be formed by welding closed an end of the capillary tube 158 to form a domed closure. An opening is then made in the domed closure by drilling, laser cutting, or electrical discharge machining (EDM) a hole of desired smaller diameter. Alternatively, a tipped or domed capillary end or formed tip 163 can be formed by attaching a metal cap to one end of a capillary by press fitting the cap to the capillary or by welding the cap in place. Either before or after attaching the cap to the capillary, a laser can be used to drill an orifice in the metal cap of a diameter that is less than the capillary's inner diameter. Another method for forming a tipped capillary by electrolytic deposition of layers of metal within a capillary tube, wherein the this method involves dipping a desired length the capillary tube into an appropriate electrolyte solution and electroplating the dipped length with metal.

The capillary tube 158 may be comprised of a metallic or non-metallic tube, however, in one preferred embodiment; the capillary tube 158 is preferably made of a nickel-based super alloy such as Inconel®. In accordance with another embodiment, the capillary tube 158 may be comprised of stainless steel or glass.

Alternatively, the capillary assembly or tube 158 may be comprised of, for example, fused silica or aluminum silicate ceramic, or other substantially non-reactive materials capable of withstanding repeated heating cycles and generated pressures and having suitable heat conduction properties may also be used. Since the heater block 150 is in thermal contact with the capillary tube 158, capillary tubes 158 with low or high electrical resistance may be used. If desired or necessary, an inside wall of the capillary tube 158 may be provided with a coating for reducing the tendency of material to stick to the wall of the capillary tube 158, which may result in clogging.

The heater block subassembly 90 also can include a ferrule 172, a capillary seal 174, an airway sleeve 176, a peek filter 178, a front filter holder 180, a back filter holder 182, an electrical connector 184, a bottom heater holder 186, a top heater holder 188, an aerosol confinement member or transition adaptor 190, and a drain tube assembly 192. The drain tube assembly 192 can include drain bag tubing 194 for the drain bag (not shown), a male connector 196 and a female connector 198. The female connector 198 is attachable to a drain bed for condensate, which has been collected by the transition adaptor 190. The bottom heater holder 186 can also include a pair of inlets 187, which are adapted to releasably engage with the bottom half of the housing 30 and communicates the output air lines 45 of the air flow controller 41 with an annular channel or gap, which is defined between the heater block 150 and the heater holder 186, 188. The heater block 150 and the heater holder 186, 188 are separated by an annular channel or gap of approximately 0.0125 to 0.50 of an inch, and more preferably an annular channel or gap of about 0.0625 of an inch.

In one embodiment, the aerosol confinement member 190 captures the aerosols produced by the capillary tube 158 of the aerosol generator 50 and directs the aerosol into the inlet end 105 of the flow tube 104. The aerosol confinement member 190 is preferably sealed to the capillary tube 158 of the aerosol generator unit 50, and allows heated air delivered to the transition adaptor 190 to be mixed with the aerosol produced by the capillary tube 158 of the aerosol generator unit 50. The aerosol confinement member 190 can include at least one baffle therein and/or a drainage port 193 at a lower end thereof adapted to attach to a condensate collection device or drain tube assembly 192.

In accordance with another embodiment, the aerosol confinement member 190 can be adapted to receive a supply of heated sheath air received from the heater block subassembly 90. The heater block subassembly 90 preferably includes at least one inlet 155 on a proximal end of the heater block subassembly 90, which receives a ventilated or hospital air supply, which is inserted into the heater block subassembly 90 and is heated or warmed by the heater block 150 forming a circumferential ring or cone of warmed air, which is admixed with the vaporized or volatized liquid formulation at the distal end of the heater block subassembly 90 within the aerosol confinement member 190. The admixing of the heated or warm air with the aerosol reduces condensation of the formulation. It can be appreciated that since the liquid formulation 136 is comprised primarily of water (up to 90% or higher; e.g., the formulation for infants can be approximately 99% water), the heated or warm air reduces the amount of condensation produced after vaporization or volatization of the liquid formulation 136. The admixing of heated air at the transition adapter 190 allows the warmer air to hold more water and moves the water-moist system away from saturated conditions, and further the additional flow rate of air further moves the moist system away from saturated conditions. Thereby condensation at and about the capillary discharge is minimized, such that condensate build-up is minimized and flow rate conditions are made conducive to remote delivery such as via the aerosol tube or flow tube 104. It can be appreciated that the air supply is preferably heated to about 125 to 145 degrees Celsius and more preferably about 135 degrees Celsius.

In accordance with one embodiment, the heater block 150 is preferably heated to about 250° C. to 300° C., and more preferably about 275° C. The hospital air flow can also be heated by passing air along the heater blocks 152, 154, or other suitable heating methods including heating the air flow with a discrete heater that is remote of the capillary tube 158, in lieu of or in addition to use of the heat generated at or about the capillary tube 158. It can be appreciated that in an alternative embodiment, the sheath air supply can be supplied without heating thereof.

In accordance with one embodiment, the source of pressurized air connected to the aerosol confinement member 190 is preferably supplied via a metering pump that drives an airstream along the heater block 150 at a predetermined flow rate in the range of about 1 L/min to 6 L/min (liters per minute).

It can be appreciated that to provide sheath air to entrain the emitted aerosol efficiently and carry it to a continuous positive airway pressure (CPAP) adaptor located at the patient. Typically, a CPAP ventilator, such as the InfantStar 950 manufactured by Puritan-Bennett of Carlsbad, Calif., creates a backpressure of approximately 6 to 10 inches $H_2O$ (water), at the continuous positive airway pressure (CPAP) adaptor. This backpressure at the adaptor requires the sheath air source to be sealed to provide control of the sheath airflow rate, which can affect aerosol delivery efficiencies. Accordingly, in accordance with one embodiment, the heater block subassembly 90 is preferably injection molded to reduce cost and inserted into the aerosol generator unit 50 with a pump as shown in FIGS. 1 and 2. It can be appreciated that by the addition of the heater block subassembly 90, a sheath air sleeve can be formed on an outer periphery of the heater block 150, such that the sheath air sleeve can be used to help distribute air more evenly around the disposable assembly housing 30 as the air is heated as the air flows over the disposable assembly housing 30.

It can be appreciated that the valve assembly 60 will include a valve control assembly, which will preferably be located inside the dual syringe pumping unit 260, such that the dual syringe pumping unit 260 and the valve control assembly will preferably be mechanically aligned. The valve control assembly will hold the part of the disposal fluid system or disposable assembly 40 that contains the disposable valve block assembly 60 and the capillary subassembly 90. The programmable automation controller will perform the control of the flow meter. A valve control box located within the base unit 20 will preferably include an access door adapted to keep the disposable closed during the operation, and to provide a means for mechanical support to hold the disposables in place inside the box. When the disposables are installed in the valve box, a secure mechanical connection can be made between a capillary ring located in the disposable to the valve control box. An electrical connection can be made from a printed circuit board (PCB) to the disposable.

The valve control box will preferably contain a plurality of drive trains or linear actuators, control valve electronics, a flow meter and a controller. The drive trains or linear actuators will preferably be four (4) in number, wherein each of the drive trains is used to control the opening and closing of the valves 116, 118, 120, 122 in the disposable valve assembly 40. In operation, the signals to open and close the valves 116, 118, 120, 122 will preferably come from the pump. The control valve electronics will consist of four linear actuators, four printed circuit boards (PCB's), and a stepper drive, which can be driven from a 15V or a 24V power supply. In operation, the pump will preferably generate speed, direction, and an enabling signal for each stepper drive. The system 10 will also include an electrical connection between the stepper drives and each actuator. The flow meter and a controller can be used to take the air from an outside source and control it before it enters the disposable valve assembly.

The system 10 can also include at least two LED fluid sensors to monitor the flow in the output lines on the disposable valve assembly 60. One printed circuit board (PCB) for controlling the LED's. The system 10 also preferably includes a safety device for ensuring and monitoring that the door is closed, and a safety device for ensuring and monitoring that the aerosol tube is connected at the end of the capillary. The heating of the capillary tube 158 will be controlled by any suitable microprocessor or programmable automation controller (PAC), such as the Compact RIO sold by National Instruments®.

Figure 8A:
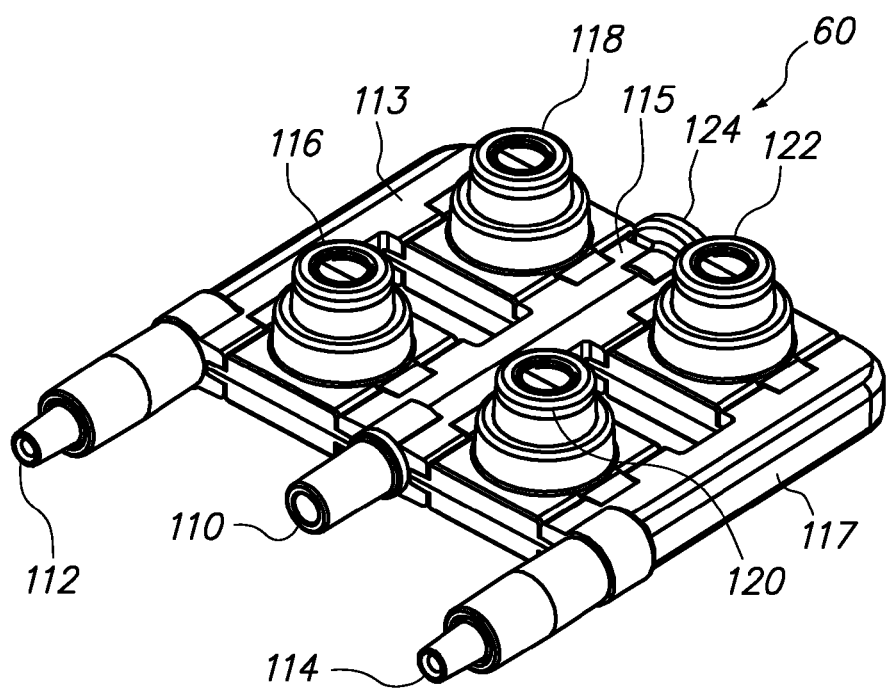
FIG. 8A is a perspective view of the valve assembly of the disposable assembly of FIG. 5.

FIG. 8A shows a perspective view of the valve assembly 60. As shown in FIG. 8, the valve assembly 60 is comprised of an inlet 110 in the form of an input barb fitting, a pair of tubing adaptors 112, 114, a plurality of valves 116, 118, 120, 122, and an outlet or output port 124. The valve assembly 60 also includes a plurality of flow channel supports 113, 115, 117, which are attached to the pair of tubing adaptors 112, 114, the plurality of valves 116, 118, 120, 122, and the outlet or output port 124.

Figure 8B:
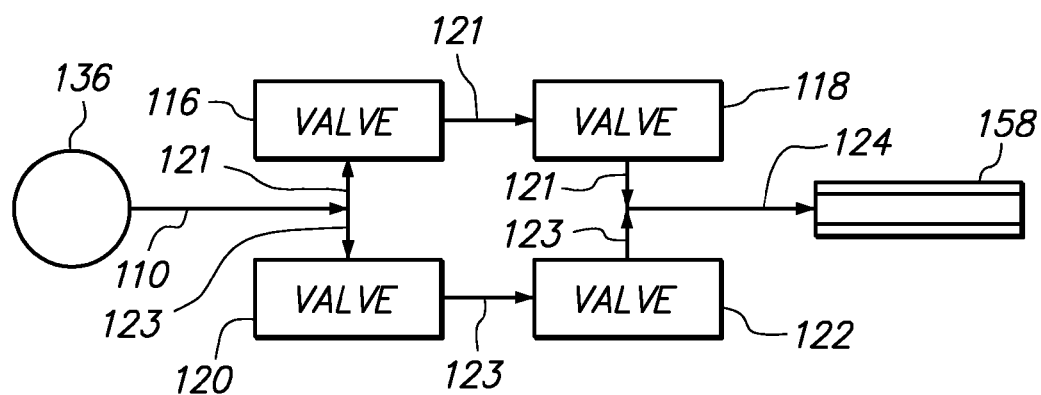
FIG. 8B is a schematic diagram of the valve assembly.

FIG. 8B shows a schematic diagram of a pumping unit and valve assembly 60. The valving arrangement or valve assembly 70 includes an inlet 110, which can be connected to a source of a liquid formulation 136, first and second flow paths 121, 123 in fluid communication with the inlet 110, and an outlet 124 in fluid communication with an inlet of the aerosol generator unit 50. As shown in FIG. 8B, the first and second valves 116, 120 are located along the first flow path 121, and the third and fourth valves 118, 122 are located along the second flow path 123. In accordance with one embodiment, the valves 116, 118, 120, 122 are arranged such that the first flow path 121 supplies liquid formulation 136 to the first syringe pump when the first valve 116 is open and the second valve 118 is closed, while the second flow path 123 supplies liquid formulation 136 to the second syringe pump when the third valve 120 is open and the fourth valve 122 is closed. The first flow path 121 also supplies liquid formulation 136 to the aerosol generator unit 50 when the first valve 116 is closed and the second valve 118 is open. In addition, the second flow path 123 supplies liquid formulation to the aerosol generator unit 50 when the third valve 120 is closed and the fourth valve 122 is open.

Figure 8C:
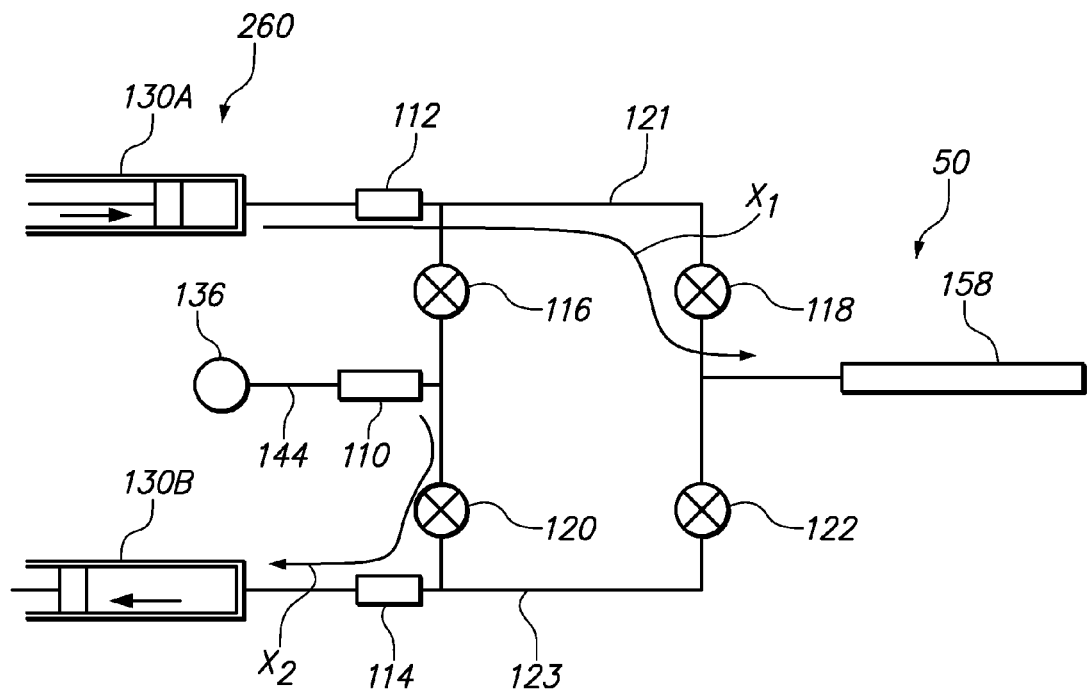
FIGS. 8C-8E are schematic diagrams of the valve assembly and the syringe pumps in accordance with an embodiment.
Figure 8D:
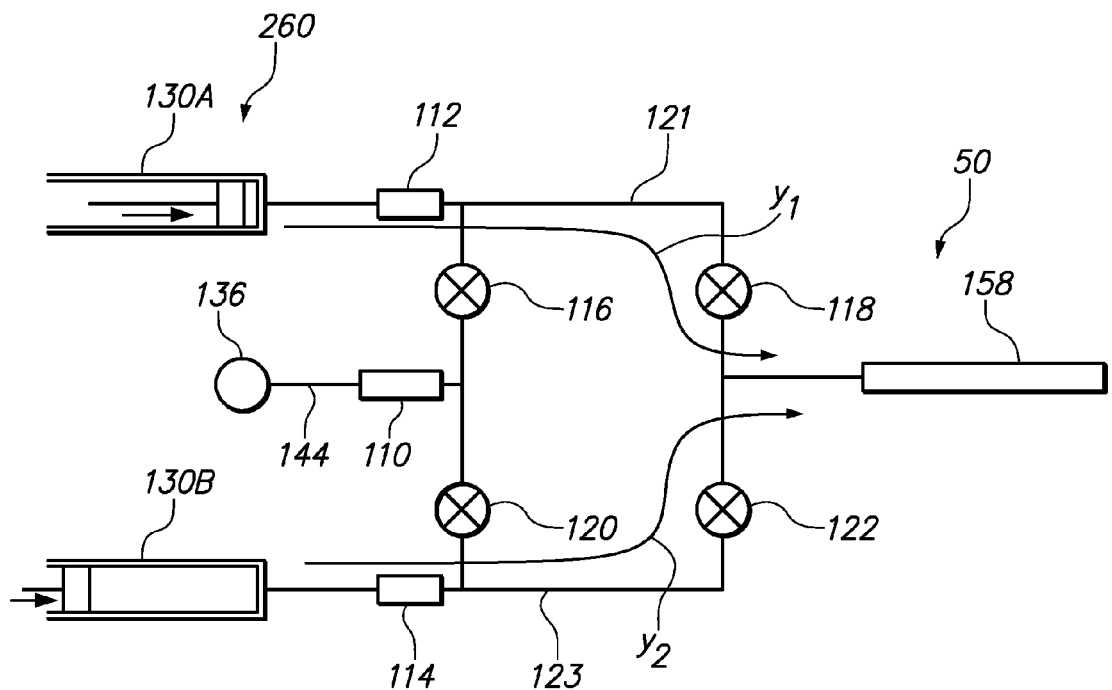
Figure 8E:
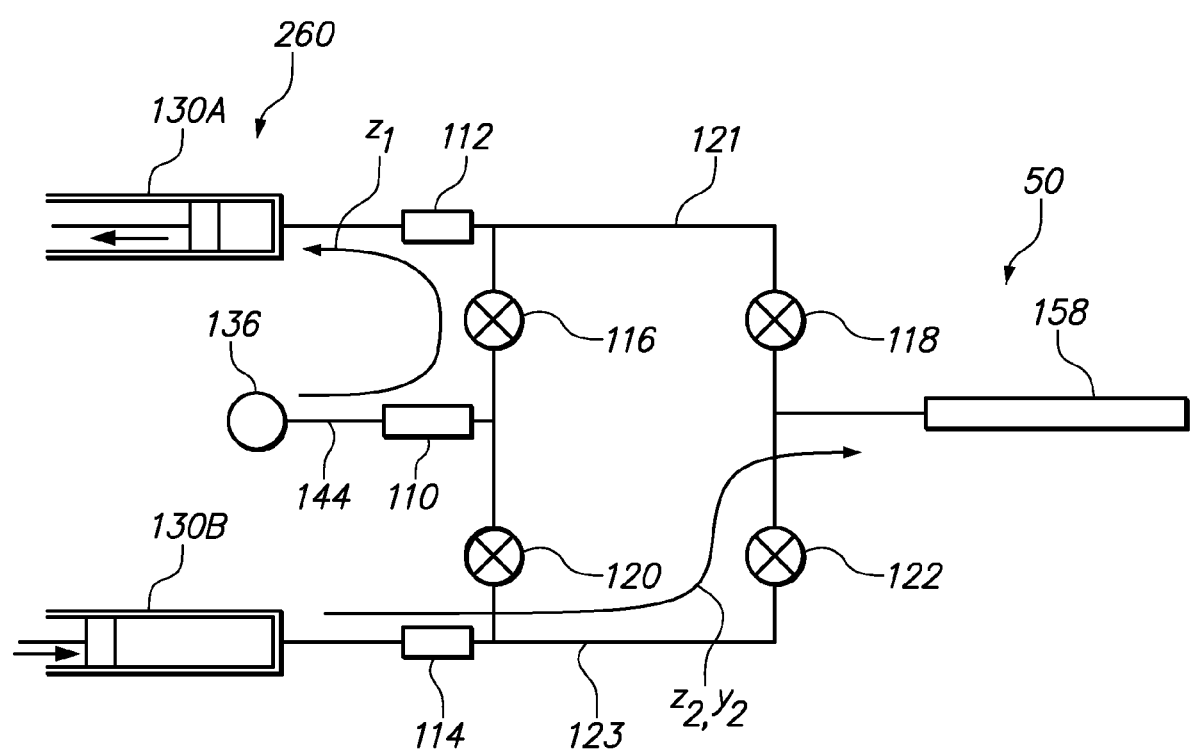

More particularly, now referring to FIGS. 8C, 8D and 8E, the first and second syringe pumps 130a and 130b are alternately communicated with the capillary 158 of the aerosol generator system 50 during their respective delivery strokes and alternately are communicated with the fluid (formulation) source 136 during their respective drawing (aspirating) stokes, with all such actions being executed in cooperation with valves 116, 118, 120, 122.

Referring specifically to FIG. 8C, when the first syringe pump 130a is discharging, its output is directed along a flow path "x1" from the first syringe pump 130a to the capillary 158. The flow path x1 is established by closure of the valve 116 and the opening of valve 118. At the same time, the second syringe pump 130b is executing its aspirating stroke to draw fluid from the source 136 through channel 144 and inlet 110 along a path designated "x2" in FIG. 8C. In order to establish this flow path x2, the valve 120 is opened and the valve 122 is closed.

Referring to FIG. 8D, the system is approaching the end of the discharge stroke of the first syringe pump 130a; and in accordance with handshake parameters, the system is executing at the same time for a brief period simultaneous initiation of a new discharge stroke in syringe pump 130b. In this mode, the output of the first syringe 130a is directed a long the first flow path "y1" to the capillary 158 which is established by closure of the valve 116 and the opening of the valve 118. Likewise, the output of the second syringe pump 130b is directed along a path "y2" to the capillary 158 via closure of the valve 120 and the opening of the valve 122.

Referring now to FIG. 8E, the first syringe pump 130a is executing its aspiration stroke wherein formulation is drawn from the fluid source 136 along a path "z1" which is established by the opening of valve 116 and closure of valve 118. At the same time the second syringe 130b continues to execute its discharge stroke to supply the formulation along a path to "z2" to the capillary 158 via closure of valve 120 and the opening of the valve 122.

It is to be realized that as the second syringe pump 130b completes its discharge stroke, the first syringe pump 130a will have already completed its aspirating stroke and will have initiated its discharge stroke in accordance with handshake parameters. At that point the flow through the system will resemble that shown in FIG. 8D, except that the first syringe pump 130a will be in initiating its discharge stroke and the second syringe pump 130b will be just completing its discharge stroke.

It can be appreciated that when dispensing certain liquids through the capillary passage, with or without the intent to aerosolize, the properties of the liquid or liquid formulation may cause a coating, agglomeration, or deposits to form on the inside the capillary passage 158. In addition, accumulation of such material within the capillary or capillary passage can also lead to clogging of the capillary or capillary passage. Accordingly, it would be desirable to have a system and method of modulating or changing the flow of the liquid formulation periodically to enable a cleaning or flushing of any potential material within the system. The modulating or changing of the flow of the liquid formulation can also maintain a stable nominal operating pressure for the system and provide a reliable aerosol of consistent quality.

In accordance with one embodiment, an aerosolization system or drug delivery system 10 having improved reliability and the robustness of a capillary aerosol generation system, can be obtained by modulating or changing the flow of the aqueous or liquid formulation 50 for a short duration to enable cleaning or flushing of any potential material within the capillary passage or capillary tube 158. In an aerosolization system or drug delivery system 10 as shown in FIG. 7, the capillary passage and/or capillary tube 158 is heated. When the aerosol is generated, the system 10 can generate significant backpressure in the order of 1100 to 1200 psi, due to vaporization of the aqueous or liquid formulation 136 and the pumping of the vapor/liquid formulation 136 through a reduced orifice or tipped capillary at the exit of the aerosol generation unit 50. Large particles in the aqueous or liquid formulation 136, and sub optimal vaporization can also cause a gradual increase in pressure in the system up to 3000 to 3500 psi, at which point the material (or clogging particles) either is ejected from the capillary passage or irreversibly clogs the capillary passage or capillary tube 158.

In accordance with an embodiment, a method of dispensing a liquid formulation in a drug delivery system to an aerosol generation unit 50, includes the steps of dispensing a liquid formulation 136 to a pumping unit 260; supplying the liquid formulation 136 from the pumping unit 260 to a capillary tube 158 of an aerosol generation unit 50 at a first flow rate; vaporizing at least a portion of the liquid formulation 136 within the capillary tube 158 of the aerosol generation unit 50; and periodically increasing the flow rate from a first flow rate to a second flow rate. The flow rate returns to the first flow rate after each of these short durations of increased flow. In accordance with a preferred embodiment, the second flow rate is preferably at least twice the first flow rate. It can also be appreciated that the by increasing the flow rate within the system 10, the system 10 experiences an increase in the operating pressure within the capillary passage of the aerosol generation unit 50.

In use with the system 10 as shown in FIG. 7, an example of a system and/or method of dispensing a liquid formulation 136 to maintain a clog free capillary can be achieved by periodically increasing the flow rate from a pumping unit 260 to an aerosol generation unit 50 with a defined pump cycle. In accordance with one embodiment, a clog free capillary passage can be achieved by the cleaning or flushing of any potential material within the capillary or capillary passage by increasing the flow rate (i.e., the first flow rate, e.g., 20 microliters per second) from the valving assembly 60 to a second flow rate. In accordance with one embodiment, the second flow rate is at least two times the first flow rate (i.e., approximately 40 microliters per second). In addition, the increased flow rate is preferably for a short duration (i.e., two (2) to four (4) seconds for a pump cycle of approximately 50 seconds).

In a preferred embodiment, the periodic increase in flow rate within the capillary or capillary passage does not include any reduction in pressure within the capillary. It can be appreciated that a reduction in pressure within the capillary can lead to clogging of the capillary. Accordingly, the increase in flow rate preferably coincides with the maintenance of the pressure within the capillary and/or an increase in pressure within the capillary tube 158.

For example, in accordance with one embodiment, the pumping unit 260 dispenses the liquid formulation 136 at approximately 20 microliters per second ($\mu$l/s) to a valving assembly 60 for delivery to the capillary passage or capillary tube 158. The valving assembly 60 includes a pair of syringes 130, wherein one syringe dispenses for fifty seconds, after which it refills and the other syringe dispenses for fifty (50) seconds. Thus, the natural periodic handshake of syringes every fifty (50) seconds can be taken advantage of as a convenient opportunity to increase the liquid formulation 136 flow rate from 20 to 40 microliters per second ($\mu$l/s) for a short duration.

In accordance with another embodiment, the increase in flow rate can be accomplished by dispensing from the second syringe while the first syringe is still dispensing. In particular, an overlap or increase in flow rate can occur for between two (2) to four (4) seconds. In addition to increasing or doubling the flow rate, the system 10 also preferably pressurizes the fluid or liquid formulation 136 in the syringe to a value close to the operating pressure before the syringe begins dispensing the liquid formulation 136 to the aerosol generator 50.

In an alternative embodiment, a single syringe pump unit 130 can be used, wherein the flow rate is increased as part of the delivery cycle. In accordance with a single syringe pump system, the system 10 has a defined fill cycle, upon which a short burst or periodic increase in the flow rate increases the operating pressure and ejecting any material that may be accumulated inside the capillary or capillary passage.

It can be appreciated that the timing of the periodic increase in flow can be a function of the properties or concentration of the liquid material or formulation 136, the flow rate, and the aerosolization parameters. For example, a liquid material or formulation 136 having a higher concentration (of medicaments or other materials) will preferably require more frequent increases in flow rate (i.e., flushes) than a liquid formulation 136 having a lower concentration.

In accordance with another embodiment, the modulating or changing of the first flow rate to a second flow rate can be performed in a plurality of short bursts, wherein each of the plurality of short bursts occurs for less than one second at a frequency of one burst every 10 seconds or less. In addition, it can be appreciated that by increasing the flow rate, an increase of 10 to 20 percent in the operating pressure within the system can be achieved, which can prevent the build up of any significant amount of large accumulation inside the capillary tube 158.

Figure 9:
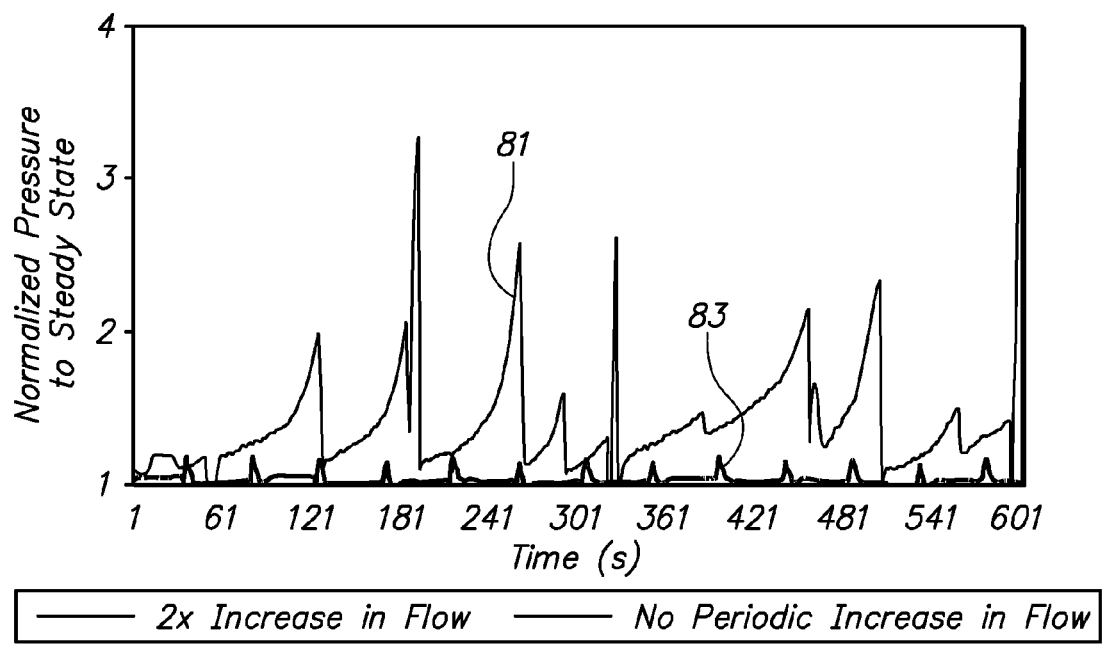
FIG. 9 is a chart showing the benefit and effectiveness of periodically increasing the flow rate.

An example of the benefit and effectiveness of a periodic increase in flow rate in an aerosolization system is shown in FIG. 9. The first plot 81 shows the typical capillary pressure behavior without any changes in flow rate. Due to any number of failure modes, such as formulation particle size, sub optimal aerosolization, etc., it can be seen that the pressure within the capillary tube 158 rises over a period of a few seconds. In accordance with one embodiment, the obstruction within the capillary tube 158 is ejected from the capillary or results in an irreversible clog. The second plot 83 shows the behavior when the flow rate is doubled every 50 seconds. The doubling of the flow rate for two (2) to four (4) seconds results in 10 to 20 percent increase in the operating pressure of the liquid formulation, which keeps the capillary clog free by preventing the buildup of any significant amount of large particles inside the capillary. The periodic increase in flow rate not only helps maintain a clog free capillary, but can also provides a stable nominal operating pressure and produces aerosols of consistent quality.

Figure 10:
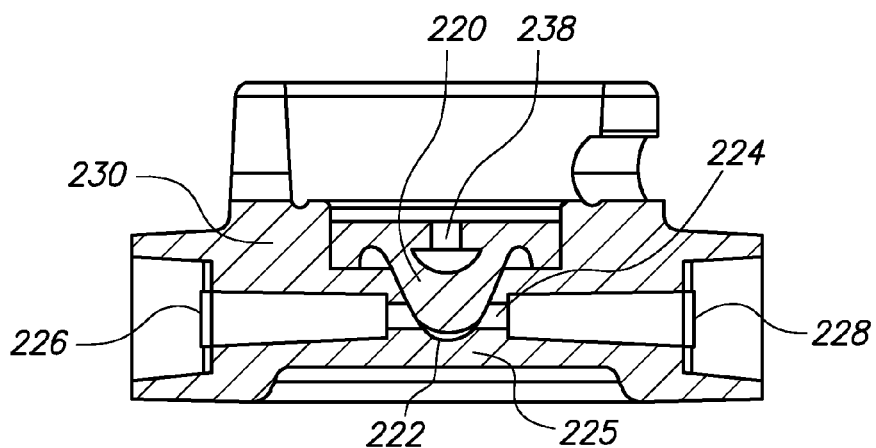
FIG. 10 is a cross-sectional view of one of the valves of the valve assembly as shown in FIG. 8A.

FIG. 10 shows a cross-sectional view of one of the plurality of valves 116, 118, 120, 122. As shown in FIG. 10, the plurality of valves 116, 118, 120, 122 are preferably comprised of a flexible membrane 220 that can be pushed down to fill an inner cavity or void 222 within a fluid passageway 224. The squeezing action plugs both an entrance or entry port 226 and the exit port 228 of the passageway 224. In addition, by keeping the cross sectional area of the entrance and exit ports 226, 228 small, the forces necessary to keep the flexible membrane 220 closed and stop the fluid flow is relatively small. The small ports 226, 228 also reduce dead volume, which improves system function by minimizing air pockets and reducing priming time.

Since the flexible membrane 220 is considerably larger than the entrance and exit ports 226, 228 it will see substantially larger forces. It can be appreciated that the flexible membrane 220 must be mechanically restrained yet allow for movement in order to fill the ridged cavity (upon closure). As shown, the membrane 220 is captured within a housing 230 that pinches an outer ring making a fluid tight seal. The inner cavity 222 has a passage so that a pusher 238 can actuate the membrane 220. A spring (not shown) can be included to assure that the membrane 220 is always open when no pressure (or vacuum) is present in the fluid lines. The spring pushes against the pusher 238, which is embedded within the membrane 220 to keep the membrane 220 in an open position. It can be appreciated that any number of valve assemblies can be used into a system to control the flow of fluid at different points in the system 10. For example, as shown in FIG. 8A, the system 10 includes a four (4)-valve assembly in conjunction with a dual syringe pump to pump fluid at a constant rate at high pressure.

Figure 11:
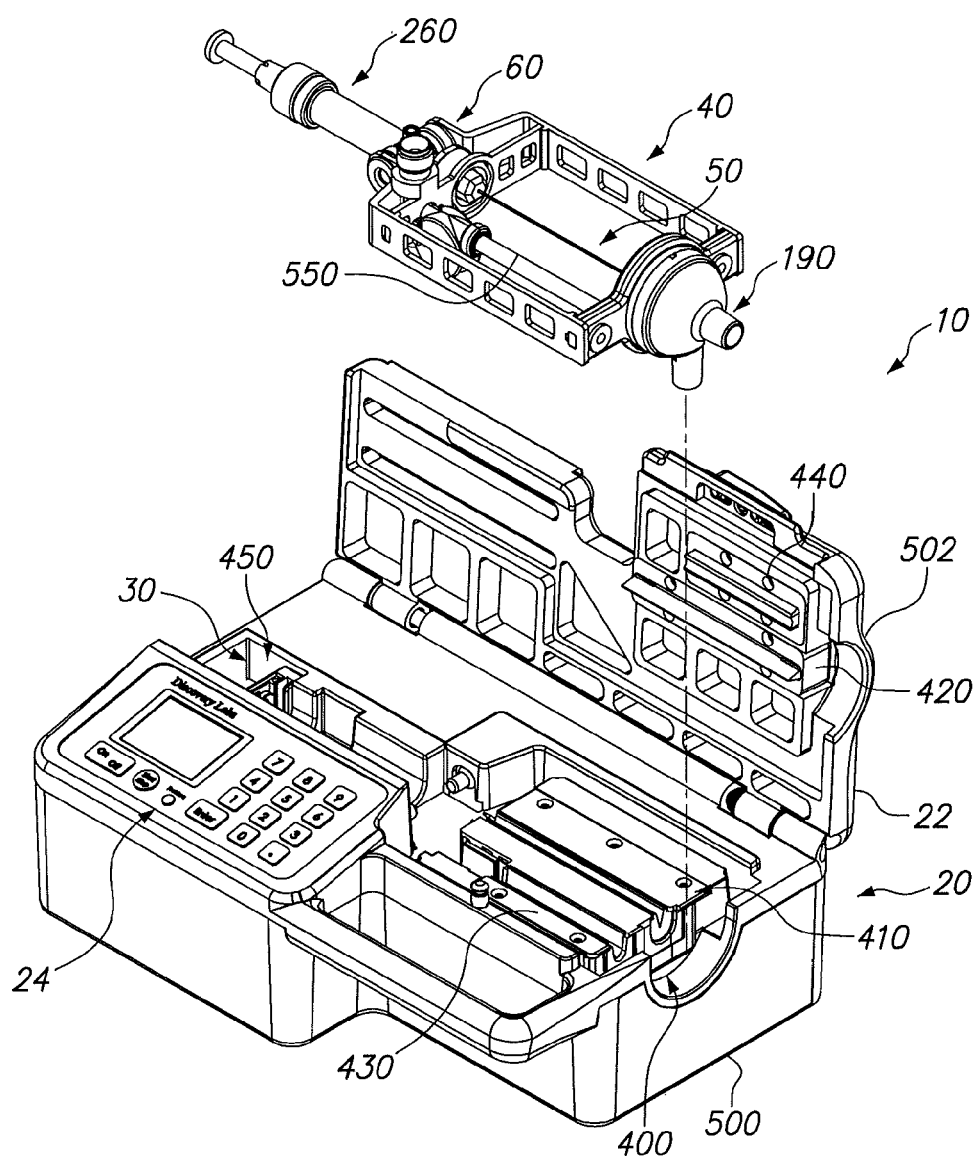
FIG. 11 is a perspective view of a drug delivery system in accordance with another embodiment.

FIG. 11 is a perspective view of a drug delivery system 10 in accordance with another embodiment. As shown in FIG. 11, the drug delivery system 10 includes a base unit 20, which is adapted to receive a disposable assembly 40 in the form of a sterile disposable fluid system. The base unit 20 is comprised of a lower assembly or base 500 and a hinged upper assembly or cover 502 (i.e., pump top assembly). The base 500 and the hinged upper assembly or cover 502 preferably include a latch mechanism or system 506, which allows the hinged upper assembly or cover 502 to be secured to the base 500 during use.

The base unit 20 includes a heater body or subassembly 400 comprised of a lower or bottom heater subassembly 410, an upper or top heater subassembly 420, a lower or bottom sheath air subassembly 430 and an upper or top sheath air subassembly 440. In accordance with an embodiment, the lower or bottom subassembly 410 and the lower or bottom sheath air subassembly 430 are housed in the base 500 of the base unit 20. The upper or top heater subassembly 420 and the upper or top sheath air subassembly 440 are housed in the hinged upper assembly or cover 502.

As shown in FIG. 11, the lower or bottom heater subassembly 410 includes a V-shaped heater core 412 having a channel or groove 413 adapted to receive the capillary tube 158 of the disposable assembly 40. The lower or bottom heater subassembly 410 also preferably includes an insulation core subassembly 414, which is preferably comprised of a two piece insulation core subassembly 414 having a first half 416 and a second half 418, at least one cartridge heater or heating unit (not shown), and a thermocouple (not shown). The at least one cartridge heater or heating unit is preferably comprised of at least two, and more preferably three cartridge heaters, which are positioned within the insulation core subassembly 414. The at least one cartridge heater and the thermocouple preferably extend longitudinally within the insulation core subassembly 414. It can be appreciated that in accordance with an alternative embodiment, the heating unit is heated coils and/or wires.

The lower or bottom sheath air subassembly 430 is preferably comprised of a sheath air insulator or insulation member 432 having a V-shaped groove or channel 434, which receives the sheath gas tube subassembly 530 (FIG. 15) of the disposable assembly 40. At least one cartridge heater or heating unit (not shown), and at least one thermocouple (not shown) are preferably longitudinally positioned within the lower or bottom sheath air subassembly 430. The heater subassembly 400 also includes a heater assembly cover 441 and a sheath assembly cover 443 to prevent dissipation of heat from the heater subassembly 400 to other parts of the system 10.

The upper or top heater subassembly 420 is preferably comprised of a wedge core 422 having a protruding V-shaped portion 424, and a top heater insulation member 426. The upper or top sheath assembly 440 is comprised of a sheath wedge core 442 with a longitudinally extending channel or groove 444, and a top sheath insulator or insulation member 446. Upon closing of the hinged upper assembly or cover 502, the V-shaped portion 424 of the upper or top heater subassembly 420, and the channel or groove 444 of the sheath wedge core 424 are in physical contact (i.e., preferably metal to metal) with the aerosol generator unit 50 and the sheath gas tube subassembly 530 of the disposable assembly 40, respectively.

In accordance with a preferred embodiment, only the lower or bottom heater subassembly 410 and the lower or bottom sheath air subassembly 430 include cartridge heaters or heating units and thermocouples, such that only the lower or bottom heater subassembly 410 and the lower or bottom air subassembly 430 are heated. Alternatively, the upper heater subassembly 420 and the upper sheath air subassembly 440 can also include heater cartridges or heating units, and thermocouples to provide heat to the upper heater subassembly 420 and the upper sheath air subassembly 440.

The heater body or subassembly 400 is preferably constructed of a thermally conductive material, such as stainless steel or other suitable material. In use, the thermally conductive material forming the heater body or subassembly 400 is heated to and maintained at an operating temperature to volatilize at least some of the liquid material within the capillary tube 158 and/or heating of the ventilator or hospital air supply within the sheath gas tube subassembly 530.

The lower assembly or base 500 and the hinged upper assembly or cover 502 also include a disposable assembly housing 30, which is adapted to receive the disposable assembly 40. The disposable assembly housing 30 is comprised of an upper or first half 32, and a lower or second half 34. During use, the disposable assembly 40 fits within the lower or second half 34 of the disposable assembly housing 30 to ensure that the components of the disposable assembly 40 are matched to their respective connections within the disposable assembly housing 30. The lower assembly or base 500 is comprised of a housing 22, which houses the compact reconfigurable input/output (I/O) controller assembly (not shown) and an external user interface 24.

The housing 22 also preferably houses the electric components, printed circuit boards (PCB), power source, flow controllers, thermocouple devices and controls, voltage control coil, motors, fans to cool the unit, and other related digital and electronic devices for operation of the drug delivery system 10. In accordance with one embodiment, the user interface 24 can include a digital display and keypad as shown in FIG. 1, a touch pad as shown in FIG. 1, or other suitable interface system for input of information and receiving of operational data from the system 10.

Figure 12:
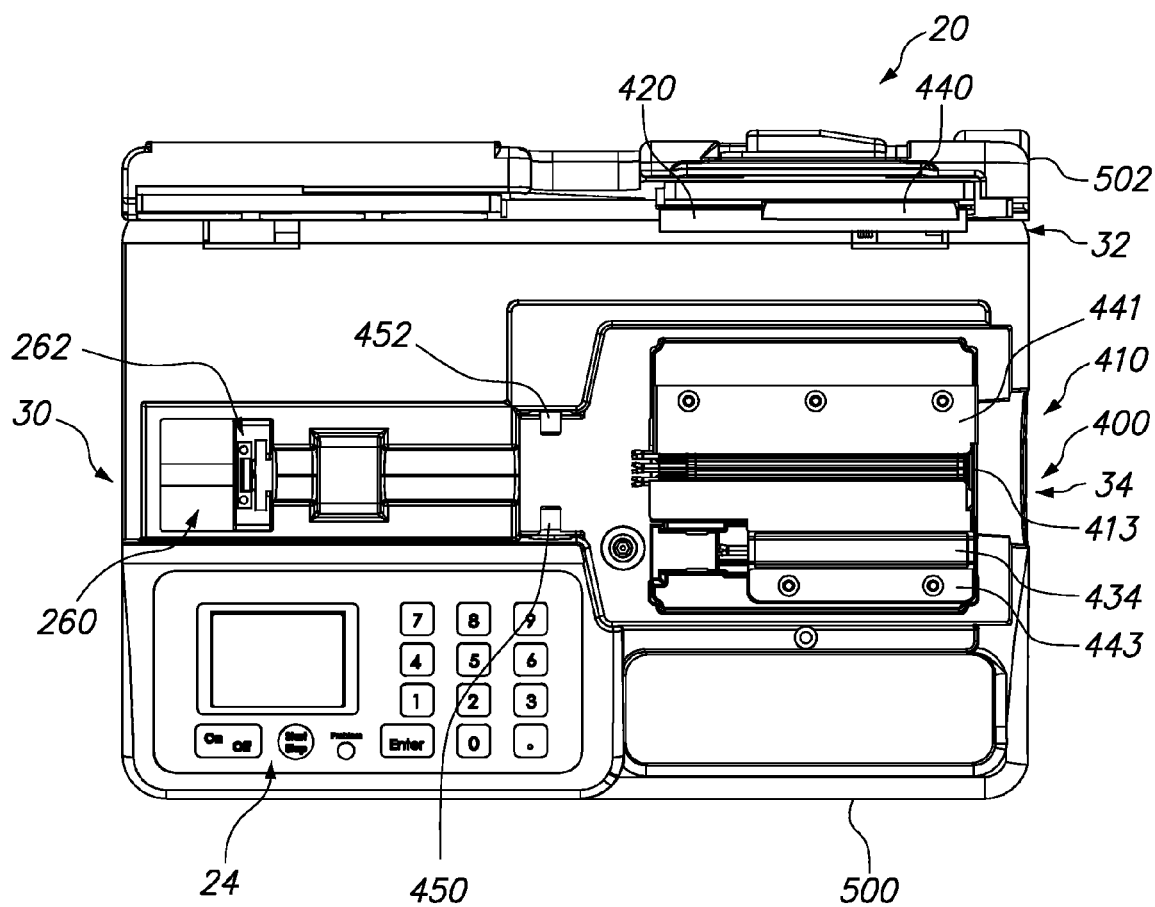
FIG. 12 is a top view of the base unit of the drug delivery system of FIG. 11.
Figure 13:
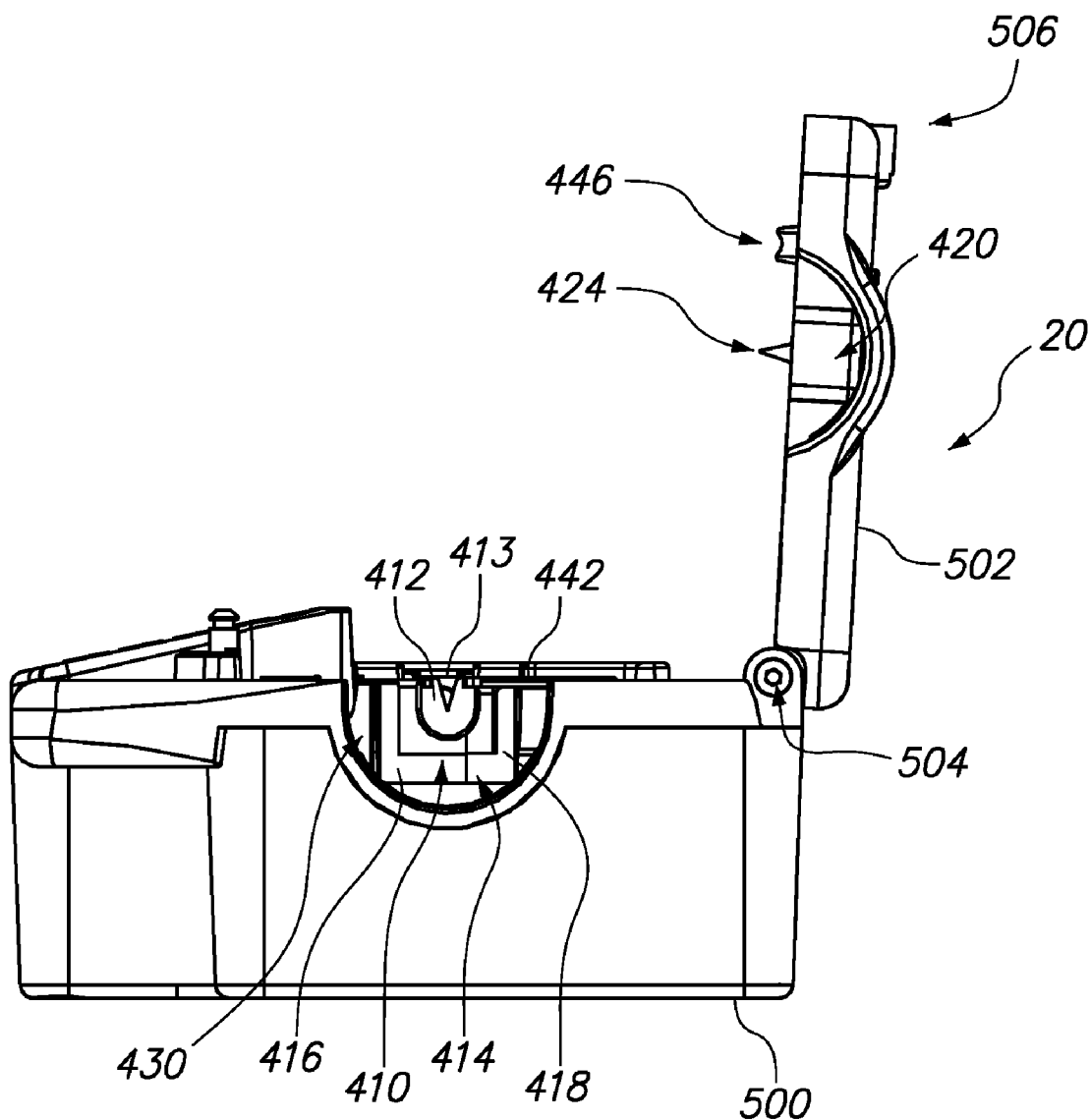
FIG. 13 is a side view of the base unit of the drug delivery system of FIG. 11.
Figure 14:
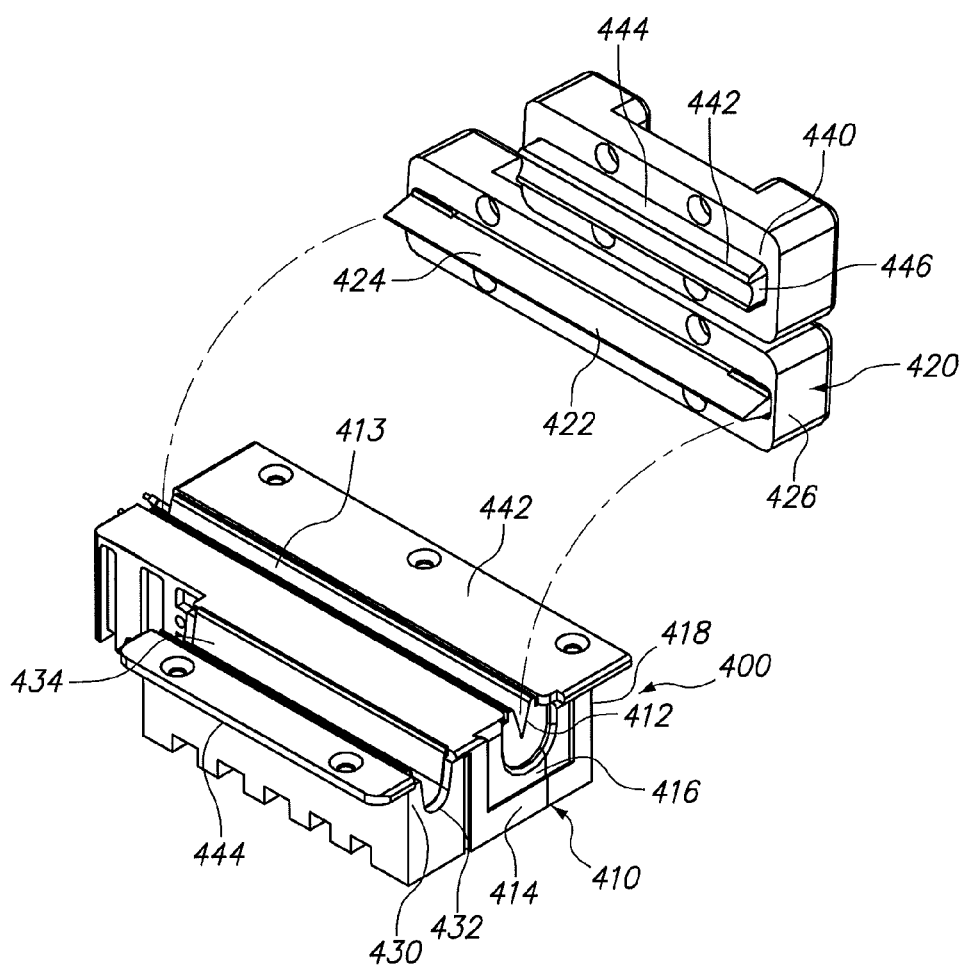
FIG. 14 is a perspective view of the heater body or subassembly of the drug delivery system of FIG. 11.

FIG. 12 is a top view of the base unit 20 of FIG. 11 with the hinged upper assembly or cover 502 in an open position. In accordance with an embodiment, the disposable assembly housing 30 in the base unit 20 is comprised of an upper or first half 32 and a lower or second half 34, which is adapted to surround the disposable assembly 40 in a clam-shell configuration. The disposable assembly 40 fits within the lower or second half of the housing 30, and ensures that the components of the disposable assembly 40 are matched to their respective connections within the base unit 20. In accordance with one embodiment, the housing 30 includes a pair of valve guides or seats 450, 452.

The lower portion 32 of the disposable assembly housing 30 also includes a control system (not shown), which activates the pumping unit 260. As shown in FIG. 12, the pumping unit 260 includes a syringe pump 262, which is housed in the disposable assembly housing 30. It can be appreciated that pump parameters such as dispense rate, aspiration rate, handshake parameters, etc. will preferably reside local to the pump and can be changed by an independent user interface such a laptop computer or other suitable input device. In use, the heater assembly 400 encases the aerosol generator (or aerosol generating unit) 50 and sheath gas tube subassembly 530, for heating a liquid material or liquid formulation 136, which is pumped through the aerosol generator unit 50 by the pumping unit 260, and heating a ventilator or hospital air supply, respectively.

FIG. 13 is a side view of the base unit 20 of the drug delivery system of FIG. 11. As shown in FIG. 13, the base unit 20 includes a base 500 and a hinged cover 502, which are attached to one another via at least one hinge 504, and more preferably a pair of hinges 504, a latching mechanism 506 and the heater body or subassembly 400.

FIG. 14 is a perspective view of the heater body or subassembly 400 of the drug delivery system of FIG. 1. As shown in FIG. 14, the heater body or subassembly 400 includes a lower or bottom heater subassembly 410, an upper or top heater subassembly 420, a lower or bottom sheath air subassembly 430 and an upper or top sheath air subassembly 440. The lower or bottom heater subassembly 410 includes a V-shaped heater core 412 having a channel or groove 413 adapted to receive the capillary tube 158 within the disposable assembly 40. The sheath air subassembly 430 includes a sheath air insulator or insulation member 432 having a cylindrical groove or channel 434, a cartridge heater (not shown), and a thermocouple (not shown). The heater subassembly 400 also includes a heater assembly cover 441 and a sheath assembly cover 443, which prevent the dissipation of heat from the heater subassembly 400 to other parts of the system 10. The upper or top heater subassembly 420 is comprised of a V-shaped or wedge core 422 having a V-Shaped portion 424, and a top heater insulation member 426. The upper or top sheath assembly 440 is comprised of a sheath wedge core 442 with a longitudinally extending cylindrical groove or channel 444, and a top sheath insulation member 446. The cylindrical grooves or channels 434, 444 are configured to mate with the cylindrical surface of the sheath air tube 532 (FIG. 16).

FIG. 15 is a perspective view of the disposable assembly 40 of the drug delivery system of FIG. 11. As shown in FIG. 14, the disposable assembly 40 includes a syringe assembly 70 comprised of a syringe 130, a valving arrangement or valve assembly 60 comprised of a pair of valves 120, 122, an aerosol generator unit 50 having a capillary tube 158, a sheath gas tube subassembly 530, and an aerosol confinement member or transition adapter 190. The disposable assembly 40 also includes a pair of support members 560, 562, which are attached at one end to the syringe assembly 70/valve assembly 60 and at the other end to the aerosol confinement member or transition adapter 190. The aerosol confinement member or transition adapter 190 is preferably attached to at least one condensate collector or fluid trap assembly 100 as shown in FIG. 7, which includes a bowl or fluid trap 102, a bowl top 103 for the fluid trap 102, and tubing or flow tube 104. The tubing or flow tube 104 is attachable to an additional tubing section (not shown), which is attachable to a patient interface in the form of a CPAP adaptor, nosepiece or mouthpiece.

In accordance with an embodiment, as shown in FIG. 15, the disposable assembly 40 preferably includes a syringe assembly 70 comprised of a single (i.e., one) syringe 130, and valve assembly comprised of a pair of valves 120, 122, which are operable to supply a liquid formulation 136 (FIG. 5) into a feed tube end or proximal end 160 of the capillary tube 158 of the aerosol generator unit 50. As shown in FIG. 15, the pair of valves 120, 122 is preferably located perpendicular to the syringe 130 and the capillary tube 158.

In accordance with one embodiment, the pumping unit 260 should be able to support backpressures of up to at least 2,000 psi, and more preferably up to 3,000 to 4,000 psi. In accordance with one embodiment, the plunger or rod 580 of the syringe 130 is adapted to fit within the syringe pump 262 of the pumping unit 260. In addition, the syringe pump 262 is preferably mounted in a fluid resistant enclosure, and can include a force sensor on the syringe-mounting bracket to monitor the plunger force during fluid delivery.

In accordance with one embodiment, the syringe assembly 70 preferably is comprised of a syringe barrel or body 588 (FIG. 16) capable of dispensing approximately 100 microliters to 2000 microliters of liquid material or liquid formulation 136 per pump cycle from a container closure system 350, and more preferably about 500 microliters to 1000 microliters of liquid material or liquid formulation 136. It can be appreciated that the single syringe assembly 70 as shown in FIGS. 11-16 provides a high pressure drug delivery system 10 with almost continuous delivery. In accordance with one embodiment, the single syringe 130 dispenses a volume of approximately 500 micro-liters to 1000 micro-liters per pump cycle with an aspiration time of less than 5% of the total pump cycle.

The disposable assembly 40 also includes an inlet 536 adapted to receive a ventilated or hospital air supply, which is fed to the sheath gas tube subassembly 530. The ventilated or hospital air supply is heater or warmed by the sheath air subassembly 430, which is admixed with the vaporized or volatized liquid formulation (i.e., generated aerosol) at the distal end 162 of the capillary tube 158 within the aerosol confinement or transition adapter 190.

FIG. 16 is an exploded view of the disposable assembly 40 of FIG. 15. As shown in FIG. 16, the disposable assembly 40 includes a syringe assembly 70 having a single syringe 130, a valve assembly 60 having a pair of valves 120, 122, an aerosol generator unit 50, and an aerosol confinement or transition adapter 190.

The syringe assembly 70 is preferably comprised of a single syringe 130 comprised of a plunger 580, a test cap 582, an alignment member 584, a plunger seal 586, and a syringe body 588 having a pair of valve seats 589. Each valve 120, 122 includes a disposable valve membrane 592, a threaded membrane plug 590, and a membrane pusher 540. At a distal end of the syringe body 588, the syringe assembly 70 includes a filter 542 (preferably stainless steel), which is adjacent to a pressure drop assembly comprised of an upstream housing member 544, a downstream housing member 548 and a pressure drop disk 546 positioned therein. The disposable assembly 40 also includes an air control nut 550, an air controller base member 552, a ferrule 554, a feed tube nut 556, a domed capillary tube 158, a capillary end member 570, a two piece end holder 572, 574, and an aerosol confinement or transition adapter 190. A pair of support members 560, 562 is attached at one end to the syringe assembly 70/valve assembly 60 and at the other end to the aerosol confinement member or transition adapter 190. In addition to providing structure for the syringe assembly 70, the capillary tube 158, the sheath air tube subassembly 530, and the aerosol confinement or transition adapter 190, the support members 560, 562 also ensure that the components of the disposable assembly 40 are matched to their respective connections within the base unit 20.

The disposable assembly 40 also includes a sheath air tube subassembly 530 comprised of a sheath air tube 532 having an inlet 534 and an outlet 536, and a turbine assembly 538. The turbine assembly 538 controls the amount of flow of ventilated or hospital air supply to the aerosol confinement or transition adapter 190 through a valve assembly (not shown). In accordance with an embodiment, the turbine assembly 538 regulates the flow rate of the ventilated or hospital air supply by transmitting the rotation velocity of the turbine assembly 538 in revolutions per minute (RPM) to the controller assembly 36, by opening, closing or at least partially obstructing the passage within the valve assembly to increase or decrease the flow rate and/or supply of ventilated or hospital air supply to the sheath air tube subassembly 530.

In accordance with an embodiment, the capillary tube 158 is a domed capillary tube, which includes a feed tube end or proximal end 160, and a domed capillary end or distal end 162. The capillary tube 158 in accordance with an embodiment, preferably has an inside diameter in the range of about 0.05 to 0.53 millimeters, and more preferably in the range of about 0.1 to 0.2 millimeters. The feed tube end 160 is preferably circular in cross-section with a domed capillary end 163 on the distal end 162 of the capillary tube 158. A particularly preferred inside diameter of the capillary tube 158 is approximately 0.1905 mm (or 0.0075 inches). In accordance with one embodiment, the capillary tube 158 is a tipped capillary as described in U.S. Publication No. 20050235991, the contents of which are hereby incorporated by reference in their entirety.

Figure 17:
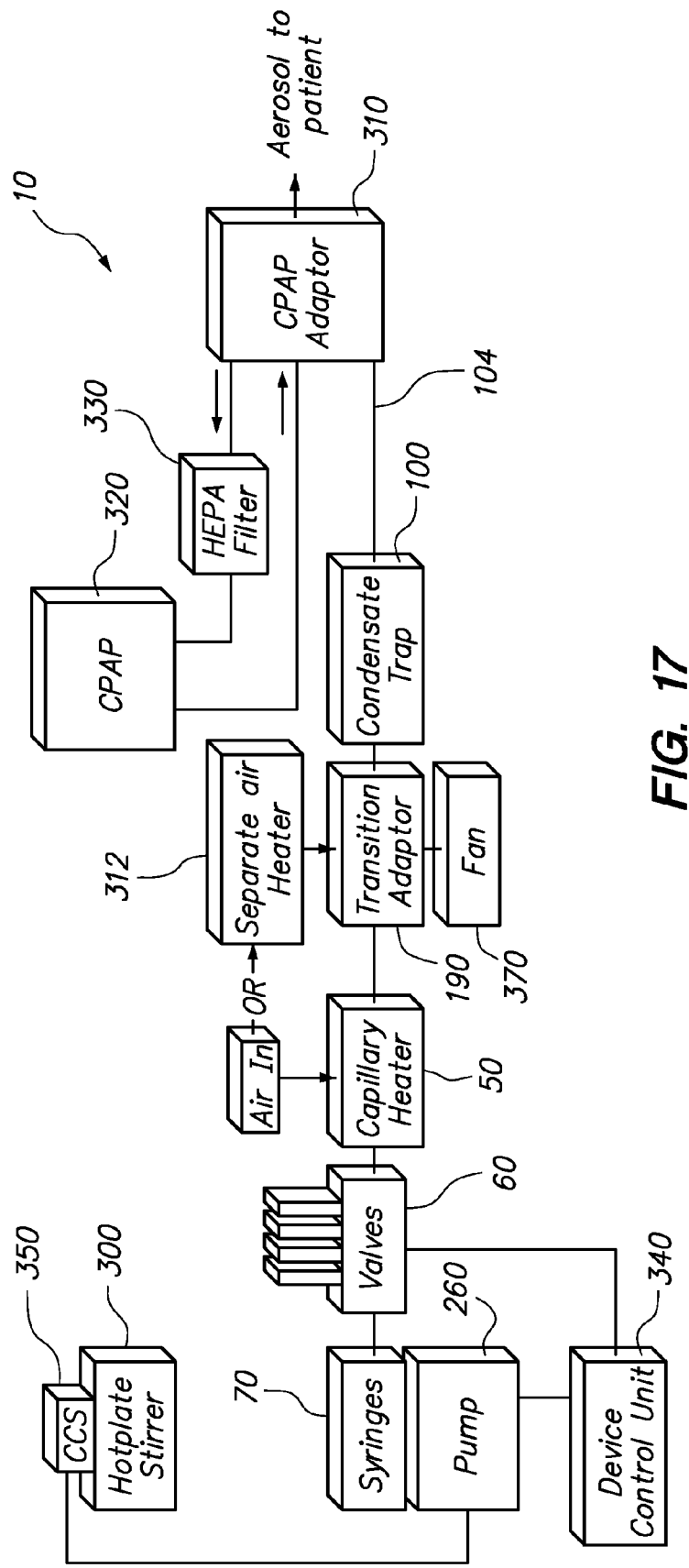
FIG. 17 is a block diagram of a drug delivery system in accordance with an embodiment.

FIG. 17 shows a diagram of the drug delivery system 10. As shown in FIG. 17, the drug delivery system comprises a formulation or dose packet 350 (or closed closure system), a hot plate/stirrer 300, a pumping unit 260, a syringe assembly 70, a valve assembly 60, an aerosol generator unit 50 having a heater block 150 and a capillary tube 158 therein, a transition adaptor 190, and a condensate trap 100. The system 10 also can include a CPAP adaptor 310 for delivering an aerosol to a patient, an air filter 330 (such as a HEPA filter), a source of air (CPAP) 320, and a control unit 340. The source of air 320 is preferably from a hospital compressed airline or pressurized air source, such as a tank of compressed air with a suitable valve arrangement to achieve a desired air flow.

In accordance with one embodiment, a liquid material or liquid formulation 136, such as Surfaxin®, which is contained within a formulation or dose packet 350 is prepared for delivery to a patient by initially heating the packet 350 on the hot plate/stirrer 300 to liquefy the formulation to a desired viscosity (i.e., a highly viscous formulation) for delivery to the pumping unit 260. The pumping unit 260 and the valving assembly 60 supplies the formulation 136 from the dose packet 350 at a constant and continuous rate to the aerosol generator unit 50, which includes a capillary passage in which the liquid formulation 136 is at least partially vaporized. The heater block 150 heats the capillary passage to a temperature range effective to at least partially volatilize liquid formulation 136 in the capillary passage or tube 158 into an aerosol. The aerosol generator unit 50 also preferably includes at least one air passage arranged such that the source of air 320 is heated by the heater body or block 150, and wherein the heated or warmed air is admixed with the aerosol produced by the aerosol generator unit 50. It can be appreciated that the system 10 can include a separate air heater 312 in the form of a discrete air heater that is remote to the capillary tube 158, in lieu of or in addition to the use of the heat generated at or about the capillary tube 158.

The transition adaptor or aerosol confinement member 190 captures the aerosols produced by the aerosol generator unit 50 and the capillary tube 158 and directs the aerosol into a flow tube 104 for delivery to the patient via a CPAP adaptor 310. The CPAP adaptor 310 preferably delivers aerosols to the patient at about 38° C. to 42° C. and more preferably about 40° C. for infants. It can be appreciated that be varying the length of a delivery hose or tubing 104, the delivery temperature of the aerosols can be delivered at a suitable or desirable temperature. The aerosol confinement member 190 is preferably sealed to the aerosol generator unit 50 or capillary tube 158, which prevents ambient air (in contrast to heated air delivered to the transition adaptor) from admixing with the aerosol produced by the aerosol generator unit or capillary tube 158. The transition adaptor or aerosol confinement member 190 can include a condensate trap 100 having at least one baffle therein and/or a drainage port at a lower end thereof adapted to attach to a condensate collection device or drain tube assembly. The admixing of the heated or warm air with the aerosol produced by the formulation reduces the amount of condensation from the capillary tube 158 to be able to deliver an aerosol to the patient located at a remote location from the system 10 and the aerosol generating unit 50.

In accordance with another embodiment, a cool air supply from a fan or other suitable cooling device 370 can be used to cool the flow tube 104 attached to the continuous positive airway pressure (CPAP) adaptor 310 or other suitable device. The fan or other suitable cooling device 370 is preferably located below the transition adapter 190. A thermocouple or temperature monitoring device (not shown) located within the patient interface device or CPAP adaptor 310 monitors the temperature of the admixture of heated or warm air with the generated aerosol. The temperature of the admixture of heated air and generated aerosol is then fed to a temperature controller (not shown) located outside of the base unit 20, or alternatively to a temperature controller located within and which is an integral part of the base unit 20. During operation of the system, the temperature controller controls the fan or other suitable cooling device 370 to initiate cooling or a reduction in the temperature of the mixture of the heated air and the generated aerosol in response to the temperature of the heated air and generated aerosol at the patient interface device or CPAP adaptor 310. In accordance with an embodiment, the cooling of the heated air and the generated aerosol from the aerosol generator unit 50 can be performed by increasing the fan speed.

The system 10 preferably in drug delivery applications is adapted to provide an aerosol having average mass median particle diameters of less than 3 microns, and more preferably an average mass median particle diameter of less than 2 microns to facilitate deep lung penetration. In accordance with a preferred embodiment, the aerosol has an average mass median particle diameter of between about 0.2 to 2 microns and more preferably an average mass median particle diameter of about 0.5 to 1.0 microns. It is also desirable, in certain drug delivery applications, to deliver medicaments at high flow rates, e.g., above 1 milligram per second. It can be appreciated that the source of liquid formulation preferably contains a lung surfactant adapted for delivery as an aerosol to an infant's lungs. For example, in accordance with one embodiment, the liquid formulation is a medicament to treat Respiratory Distress Syndrome (RDS) in infants.

Figure 18:
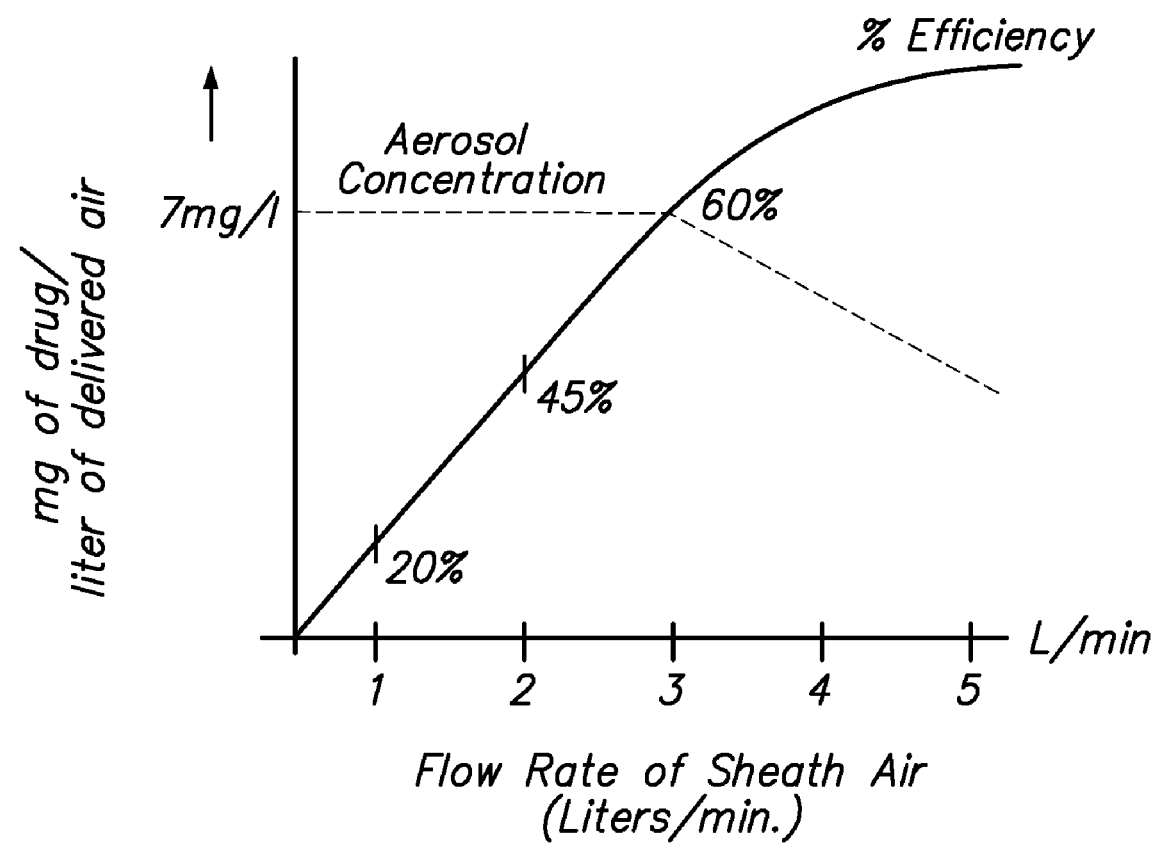

In accordance with an embodiment, the system 10 is preferably capable of delivering an aerosol with a drug concentration of 2.3 milligrams per liter of air from a liquid formulation with a drug concentration of 10 milligrams per milliliter (mg/ml) and commensurately higher aerosol concentrations from formulations with higher concentrations. In addition, it is noteworthy that the aerosol generator and/or system 10 as shown achieves a uniquely high aerosol concentration for a give initial liquid formulation. For example, as shown in FIG. 18, which is representative of expected results, which could vary, in accordance with an embodiment, a drug concentration of 30 milligrams of drug per milliliter of formulation (mg/ml), one may achieve a delivered drug aerosol concentration of 7 milligrams of drug aerosol per liter of air (mg/l) at a sheath air flow rate of 3 liters per minute (L/min). It can be appreciated that the system efficiency as shown in FIG. 18, is the ratio of the mass or active medicant as measured upstream of the CPAP adaptor divided by the mass of the active medicant pumped into the system.

While various embodiments have been described, it is to be understood that variations and modifications may be resorted to as will be apparent to those skilled in the art. Such variations and modifications are to be considered within the purview and scope of the claims appended hereto. For example, a superheated fluid could be maintained in a superheated liquid condition until discharged from the capillary, whereupon a flash vaporization will occur.

What is claimed is:

1. A drug delivery system, comprising:
   an aerosol generator unit comprising (i) a capillary passage adapted to at least partially volatilize a liquid formulation, (ii) at least one heater body operable to heat the capillary passage to a temperature range effective to at least partially volatilize the liquid formulation in the capillary passage, the capillary passage being fitted within the heater body, and (iii) at least one gas passage contained within the heater body and arranged such that gas is heated by the heater body to produce a heated gas;
   a pumping unit adapted to supply a liquid formulation to the aerosol generator unit;
   a flow passage having an inlet end in fluid communication with an outlet of the aerosol generator unit and an outlet adapted for connection to a patient interface which supplies ventilation to a patient's lungs;
   an aerosol transition adapter arranged to mix aerosol produced by the capillary passage with the heated gas in a manner that reduces condensation of aerosol to produce a mixed aerosol and operable to direct the mixed aerosol into the inlet end of the flow passage; and
   a control system operable to activate the aerosol generator unit and the pumping unit,
   wherein the control system is arranged to control temperatures for heating the liquid formulation and the gas, flow rates of the gas and aerosol, and mixing of aerosol with the heated gas in a manner that reduces condensation of aerosol to produce a mixed aerosol.

2. The drug delivery system of claim 1, wherein the pumping unit includes one syringe pump and a pair of valves operable to supply liquid formulation into an inlet of the aerosol generator unit.

3. The drug delivery system of claim 1, wherein the pumping unit includes two syringe pumps and a valving arrangement operable to supply liquid formulation into an inlet of one syringe pump during delivery of liquid formulation to the aerosol generator unit by the other syringe pump.

4. The drug delivery system of claim 3, wherein the valving arrangement includes an inlet which can be connected to a source of a liquid formulation, first and second flow paths in fluid communication with the inlet, an outlet in fluid communication with an inlet of the aerosol generator unit, first and second valves along the first flow path and third and fourth valves along the second flow path, the valves arranged such that the first flow path supplies liquid formulation to the first syringe pump when the first valve is open and the second valve is closed, the second flow path supplies liquid formulation to the second syringe pump when the third valve is open and the fourth valve is closed, the first flow path supplying liquid formulation to the aerosol generator unit when the first valve is closed and the second valve is open, and the second flow path supplying liquid formulation to the aerosol generator unit when the third valve is closed and the fourth valve is open.

5. The drug delivery system of claim 4, further comprising a control system operable to activate the aerosol generator unit and the pumping unit, the control system effecting initial filling of the syringe pumps via retraction of a first piston of the first syringe pump and a second of the second syringe pump while maintaining the first and third valves open and the second and fourth valves closed, delivering liquid formulation to the aerosol generator unit via advancement of the first piston while maintaining the first and fourth valves closed, activating the second syringe pump near the end of a delivery cycle of the first syringe pump via advancement of the second piston while maintaining the fourth valve open and the third valve closed, refilling the first syringe pump via retraction of the first piston while maintaining the first valve open and the second valve closed, activating the first syringe pump near the end of the delivery cycle of the second syringe pump via advancement of the first piston while maintaining the a second valve open and the first valve closed.

6. The drug delivery system of claim 1, wherein the capillary passage is a capillary tube adapted to fit within the heater body, and wherein the at least one gas passage is a tubular member adapted to fit with a sheath gas subassembly arranged such that the gas is heated by the sheath gas subassembly.

7. The drug delivery system of claim 1, wherein the aerosol transition adapter includes at least one baffle therein and/or a drainage port at a lower end thereof adapted to attach to a condensate collection device.

8. The drug delivery system of claim 1, wherein the pumping unit and aerosol generator unit includes disposable parts and reusable parts, the disposable parts including a capillary flow tube through which the liquid formulation is ejected as an aerosol and wetted parts of the pumping unit, the wetted parts including a screening member operable to trap particles in the liquid formulation above a predetermined size, the screening member located upstream of an inlet to the aerosol generator unit.

9. The drug delivery system of claim 1, further comprising a source of liquid formulation containing a lung surfactant adapted for delivery as an aerosol to an infant's lungs.

10. The drug delivery system of claim 1, further comprising a source of pressurized gas connected to the aerosol transition adapter, the source of pressurized gas supplying gas at a flow rate of about 1 to 6 L/min (liters per minute).

11. The drug delivery system of claim 1, wherein the aerosol generator unit is a disposable assembly, the disposable assembly comprising:
   a capillary tube adapted to form an aerosol when a liquid formulation in the capillary tube is heated to volatilize at least some of the liquid formulation therein;
   a syringe assembly comprised of a syringe pump and a pair of valves operable to supply the liquid formulation into an inlet of the capillary tube;
   a sheath gas tube subassembly comprised of a sheath gas tube operable to receive a ventilated or hospital gas supply; and
   the aerosol transition adapter.

12. The drug delivery system of claim 11, wherein the sheath gas tube subassembly includes a sheath gas tube and a turbine assembly, wherein the turbine assembly controls the flow of ventilated or hospital gas to the aerosol transition adapter.

13. The drug delivery system of claim 11, further comprising a disposable assembly housing adapted to receive the disposable assembly, the disposable assembly housing comprising:
   a heater body, the heater body comprising:
      a lower heater subassembly having a channel adapted to receive the capillary tube and at least one heating unit positioned longitudinally within the lower heater subassembly;
      an upper heater subassembly,
      a lower sheath gas subassembly having a channel operable to receive the sheath gas tube and at least one heating unit positioned within the lower sheath gas subassembly; and
      an upper sheath gas subassembly.

14. The drug delivery system of claim 13, wherein the disposable assembly housing further includes a syringe pump operable to the supply the liquid formulation into the inlet of the capillary tube.

15. The drug delivery system of claim 1, wherein the aerosol generator unit is capable of delivering an aerosol with a drug concentration of 2.3 milligrams per liter of gas from a liquid formulation with a drug concentration of 10 milligrams per milliliter (mg/ml) and commensurately higher aerosol concentrations from formulations with higher concentrations.

16. A disposable assembly operable to produce an aerosol, the disposable assembly comprising:
   a heater having a heater body;
   a capillary tube fitted within the heater body and adapted to form an aerosol when a liquid formulation in the capillary tube is heated by the heater to volatilize at least some of the liquid formulation therein;
   a sheath gas passage contained within the heater body and operable to receive a ventilated or hospital gas;
   an aerosol transition adapter arranged to mix aerosol produced by the capillary tube with sheath gas in a manner that reduces condensation of aerosol to produce a mixed aerosol and to direct the mixed aerosol into the inlet end of a flow passage; and
   a control system operable to activate the aerosol generator unit,
   wherein the control system is arranged to control temperatures for heating the liquid formulation and the sheath gas, flow rates of the sheath gas and aerosol, and mixing of aerosol with the heated sheath gas in a manner that reduces condensation of aerosol to produce a mixed aerosol.

17. The assembly of claim 16, further comprising at least one condensate collector adapted to collect condensed liquid or liquid produced by the capillary tube.

18. The assembly of claim 16, wherein the heater comprises a heater block in thermal contact with the capillary tube and adapted to receive the capillary tube, the heater block comprising:
   an upper assembly and a lower assembly, which encases the capillary tube;
   at least one heater cartridge positioned longitudinally within the upper assembly and the lower assembly; and
   at least one thermocouple incorporated in the heater block.

19. The assembly of claim 16, wherein the sheath gas passage includes a sheath gas tube and a turbine assembly, and wherein the turbine assembly controls the flow of gas from the ventilated or hospital gas supply to the aerosol transition adapter.

20. A base unit for generating aerosol, the base unit comprising:
   a disposable assembly having an aerosol generator unit therein;
   a disposable assembly housing adapted to receive the disposable assembly;
   a syringe pump operable to supply a liquid formulation to the aerosol generator unit;
   a heater having a heater body;
   a capillary tube fitted within the heater body and adapted to form an aerosol when the liquid formulation in the capillary tube is heated by the heater to volatilize at least some of the liquid formulation therein;
   a sheath gas passage contained within the heater body and operable to receive a ventilated or hospital gas;
   an aerosol transition adapter arranged to mix aerosol produced by the capillary tube with sheath gas in a manner that reduces condensation of aerosol to produce a mixed aerosol and to direct the mixed aerosol into the inlet end of a flow passage; and
   a control system operable to activate the aerosol generator unit and the syringe pump, such that the liquid formulation is at least partially volatilized to form an aerosol,
   wherein the control system is arranged to control temperatures for heating the liquid formulation and the sheath gas, flow rates of sheath gas and aerosol, and mixing of aerosol with the heated sheath gas in a manner that reduces condensation of aerosol to produce a mixed aerosol.

21. The base unit of claim 20, wherein the disposable assembly housing further includes a heater body comprising:
   a lower heater subassembly having a channel adapted to receive a capillary tube and at least one heating unit positioned longitudinally within the lower heater subassembly;
   an upper heater subassembly,
   a lower sheath gas subassembly having a channel operable to receive a sheath gas tube and at least one heating unit positioned within the lower sheath gas subassembly; and
   an upper sheath gas subassembly.

* * * * *